(12) United States Patent
Schubert et al.

(10) Patent No.: US 6,365,582 B1
(45) Date of Patent: Apr. 2, 2002

(54) S-SUBSTITUTE 11β-BENZALDOXIME-ESTRA-4, 9-DIENE-CARBONIC ACID THIOLESTERS, METHOD FOR THE PRODUCTION THEREOF AND PHARMACEUTICAL PREPARATIONS CONTAINING THESE COMPOUNDS

(75) Inventors: Gerd Schubert; Sven Ring; Guenther Kaufmann, all of Jena; Walter Elger, Berlin; Birgit Schneider, Jena, all of (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/622,803

(22) PCT Filed: Feb. 10, 1999

(86) PCT No.: PCT/DE99/00408

§ 371 Date: Aug. 22, 2000

§ 102(e) Date: Aug. 22, 2000

(87) PCT Pub. No.: WO99/45023

PCT Pub. Date: Sep. 10, 1999

(30) Foreign Application Priority Data

Mar. 3, 1998 (DE) .......................... 198 09 845

(51) Int. Cl.[7] .................. A61K 31/56; A61K 31/58; C07J 43/00; C07J 5/00; C07J 9/00
(52) U.S. Cl. .................. 514/179; 514/173; 540/29; 552/553; 552/595; 552/610
(58) Field of Search ................. 552/553, 595, 552/610; 540/29; 514/173, 179

(56) References Cited

FOREIGN PATENT DOCUMENTS

| EP | 0 648 778 A2 | 4/1995 |
|----|--------------|--------|
| EP | 0 648 779 B1 | 3/1997 |
| WO | 96/12494 | 5/1996 |
| WO | 96/19997 | 7/1996 |
| WO | 96/28145 | 9/1996 |

*Primary Examiner*—Barbara P. Badio
(74) *Attorney, Agent, or Firm*—Michael J. Striker

(57) ABSTRACT

Thiol esters of S-substituted 11β-benzaldoxime-estra-4,9-dien-carboxylic acids of the formula I

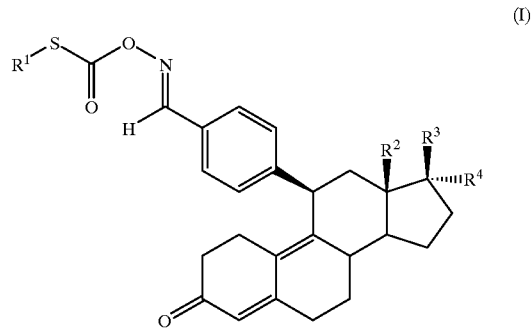

their pharmaceutically acceptable salts, a method for their synthesis and pharmaceutical preparations containing these compounds are described. These compounds bind to progesterone receptors and have distinctly reduced anti-glucocorticoid action.

25 Claims, No Drawings

S-SUBSTITUTE 11β-BENZALDOXIME-ESTRA-4, 9-DIENE-CARBONIC ACID THIOLESTERS, METHOD FOR THE PRODUCTION THEREOF AND PHARMACEUTICAL PREPARATIONS CONTAINING THESE COMPOUNDS

This application is a 371 of PCT/DE99/00408 filed Feb. 10, 1999.

BACKGROUND OF THE INVENTION

1. Field of the Invention

The present invention relates to new thiol esters of S-substituted 11β-benzaldoxime-estra-4,9-diene-carboxylic acid of the general formula I

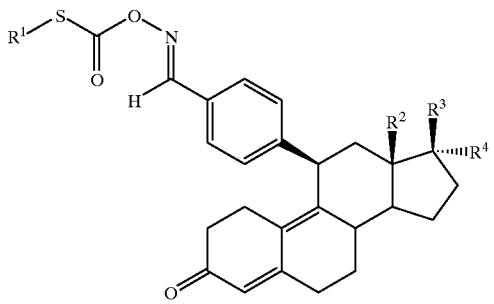

(I)

and to their pharmaceutically acceptable salts, to a method for their synthesis and to pharmaceutical preparations containing these compounds.

2. Description of the Related Art

The EP-A-0 648 778 and the EP-A-0 648 779 disclose esters, carboxylate esters and urethanes of 11β-benzaldoxime-estra-4,9-dienes. The compounds described therein have anti-progestational activity.

Anti-progestogens are steroids which, like progesterone and other progestational substances, have a high affinity for the progesterone receptor. However, they are different from these in that they do not lead to the typical physiological effects, which are brought about by the progesterone receptor. Instead, progesterone is displaced from its bonding to the receptor and its activity is inhibited. From the scientific literature, it is known that, aside from the displacement of progesterone from its binding site, malfunctions of the gene-regulatory receptor function play a decisive role here. (Klein-Hitpass, L., Cato, A. C. B, Henderson, D., Ryffel, U.: Nucleic Acid Res. 19 (1991), 1227–1234; Horwitz, K. B.: Endocrine Rev. 13 (1992) 146); McDonnell D. P.: Trends Endocrinol. Metab. 6 (1995) 133–138).

With respect to the last-mentioned aspect, known antagonists, for example ZK 98299=onapristone (DE-A-35 04 421) and RU 486=mifepristone (EP-A-0 057 115) differ at the molecular level (type I/type II antagonists) and indeed in that in the case of type I antagonists (e.g. onapristone), the hormone receptor complex no longer binds to the hormone-responsible elements or binds in a labile manner, whereas with type II (e.g. Ru 486) this is still the case (Klein-Hitpass et al.). Antigestagens which still allow receptor binding to DNA can have progesterone-like actions, while in the case of disturbance of the DNA binding of the receptor this is not possible.

Modulation of gene-regulatory activity of individual progesterone antagonists can also take place by mechanisms which initially start from the receptor protein. Various studies have demonstrated that the gene-regulatory activity of antagonist-receptor complexes is stimulated by cyclic AMP. In the presence of high concentrations of c-AMP in the tissue, activation of the antagonist-receptor complexes manifests itself; at low concentrations the receptor remains inhibited with respect to gene-regulatory activity. The occurrence of corresponding phenomena is apparently also substance-specific. The production of high c-AMP concentrations (in vitro) leads to partial agonistic action in some antigestagens; in other substances corresponding effects are, however, not caused by c-AMP (Sartorius, C A., Tung, L., Takmoto, G S., Horwitz, K B.: J Biol. Chem 268 (1993) 9262–9266; Sobek, L., Kaufmann, G., Schubert, G., and Oettel, M., 79th Annual Meeting of the Endocrine Society 1997, 3–452, 549).

Differences at the molecular level are also expressed in the pharmacodynamic behavior of progesterone antagonists. This can be demonstrated in the very different pharmacodynamic behavior of substances which are very well characterized in vivo and in vitro, such as onapristone and mifepristone (RU 486) [Elger, W., W., Neff, G., Beier, S., F ähnrich, M., Grundel, M. et al. in Current Concepts in Fertility Regulation and Reproduction, ed. Puri, C. P. and Van Look, P. F. H. (1994) 303–328.

Progesterone plays a crucial role in the control of the organ systems involved in reproductive processes. This applies to the morphological metaplastic processes in the genital tract and in the mammary gland, the regulation of hormones of the anterior pituitary lobe and of the genital organs or the inhibition and activation of parturition. These functions react with different sensitivity to progesterone. Processes which take place at very low progesterone levels deserve particular consideration with respect to the pharmacology of the antigestagens. "Pure" progesterone antagonists of type I can bring about effects which can be achieved with no [sic] dose using partial agonistic antagonists. This generally ought to be the case when the threshold for the respective effect is low, that is below the partial agonistic activity of a progesterone antagonist. Conversely, there is the possibility that under the influence of progesterone antagonists of type II, effects are observed which are caused not by the inhibition, but by the activation of the progesterone receptor. At an identical dose of this antagonist, the functions of progesterone are inhabited which proceed at high tissue concentrations.

An example of the first-mentioned case is the prostaglandin secretion of the uterus in the guinea pig during its menstrual cycle. This is stimulated toward the end of the cycle by very low progesterone levels. Only pure progesterone antagonists of type I are able to inhibit the progesterone secretion of the uterus in guinea pigs to such an extent that the reformation of the corpus luteum is completely inhibited (Elger, W., Neef, G., Beier, S., Fähnrich, M., Grundel, M., et al. in Current Concepts in fertility Regulation and Reproduction, ed. Puri, C. P. and Van Look, P. F. H. 1994 303–328). Partial agonistic substances inhibits this process little or not at all.

In the human, the progesterone antagonist RU 486 has various effects on reproductive functions which are relevant to use in therapy. This substance inhibits the action of progesterone to such an extent that when used during pregnancy the induction of an abortion occurs. This abortion- or labor-inducing property is considerably increased by simultaneous or sequential treatment with a prostaglandin (Van Look, P. F. A.; Bygdeman, M.: Oxf. Rev. Reprod. Biol. 11 (1989), 1–60; Elger, W., Neef, G., Beier, S., Fähnrich, M., Grundel, M. et al. In Current Concepts in Fertility Regulation and Reproduction, ed. Puri, C. P. and Van Look, P. F. H. 1994 303–328). Corresponding effects can be adequately explained on the basis of the pregnancy-regulating function of progesterone in pregnancy.

In addition, RU 486 and other antigestagens have effects in which the mechanism of the withdrawal of progesterone is not so clearly confirmed. This relates primarily to effects in the menstrual cycle in phases in which the progesterone levels in the blood are very low. Here, two phenomena are to be mentioned in particular, the inhibition of ovulation (Croxatto, H. B., Salvatierra; A. M.; Croxatto, H. D.; Fuentealba, A.: Hum. Reprod. 8 (1993), 201–207) and the inhibition of the estrogen-induced proliferation of the genital epithelia, in particular those of the endometrium (Wolf, J. P., Hsiu, J. G., Anderson, T. L., Ulmann, A., Baulieeu, E. E. and Hodgen, G. D.: Fertility & Sterility 52 (1989) 1055–1060). Corresponding effects are of central importance for the use of the antigestagens, in particular for antiovulatory strategies in fertility control, the reversible induction of amenorrhea, for example in the therapy of endometriosis and for the suppression of undesired estrogenic effects in the endometrium in the course of a substitution therapy with estrogens in the menopause. The coupling of the abortive and labor-inducing action with the progesterone-agonistic and in particular the antiovulatory and proliferation-inhibiting properties is of advantage for the therapeutic use of type I antagonists such as RU 486.

SUMMARY OF THE INVENTION

The object of the present invention is therefore to make available compounds which overcome the disadvantages outlined above.

The object is achieved by making available compounds of the general formula I

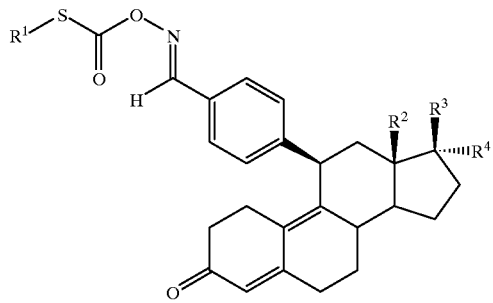

according to Claim 1 and their pharmaceutically acceptable salts and also a process for their preparation. Pharmnaceutical compositions are further made available which contain a compound of the general formula I or its pharmaceutically acceptable salt.

The present invention thus relates to S-substituted 11β-benzaldoxime estra-4,9-dienecarbonic acid thioesters of the general formula I,

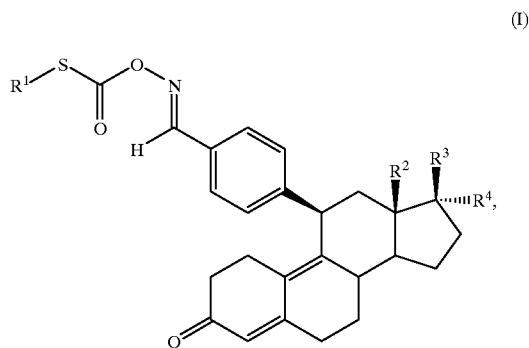

in which
$R^1$ is an alkyl radical having 1–10 carbon atoms, an aryl radical having 6–10 carbon atoms or an alkylaryl or arylalkyl radical each having 7–10 carbon atoms,
$R^2$ is an alkyl radical having 1–3 carbon atoms or a hydrogen atom,
$R^3$ is a hydroxyl group, an O-alkyl group having 1–10 carbon atoms, an O-aryl group having 6–10 carbon atoms, an O-aralkyl, or O-alkylaryl group each having 7–10 carbon atoms, a radical —$OCOR^5$, —$OCONHR^5$ or —$OCOOR^5$,
where
$R^5$ is a hydrogen atom, an alkyl group having 1–10 carbon atoms, an aryl group having 6–10 carbon atoms, an aralkyl or alkylaryl group each having 7–10 carbon atoms,
$R^4$ is a hydrogen atom, an alkyl group having 1–10 carbon atoms, an aryl group having 6–10 carbon atoms, an aralkyl or alkylaryl radical each having 7–10 carbon atoms,
a radical —$(CH_2)_nCH_2Y$,
where
n=0, 1 or 2,
Y is a fluorine, chlorine, bromine or iodine atom, a cyano, amino, azido or thiocyano group, or is a radical —$OR^6$, —$SR^6$, —$(CO)SR^6$ or —$(CO)OR^6$,
where
$R^6$ is a hydrogen atom, an alkyl group having 1–10 carbon atoms, an aryl group having 6–10 carbon atoms, an aralkyl or alkylaryl radical each having 7–10 carbon atoms,
or is a radical —$COR^5$, where $R^5$ has the meaning indicated above,
is a radical —$OR^5$ or —$OCOR^5$, where $R^5$ has the meaning indicated above,
is a radical —$(CH_2)_m$—CH=CH$(CH_2)_p$—$R^6$,
where
m=0, 1, 2 or 3,
p=0, 1 or 2 and
$R^6$ has the meaning indicated above or is a radical —$OR^5$ or —$OCOR^5$, where $R^5$ has the meaning indicated above,
is a radical —$(CH_2)_oC≡CR^7$,
where
o=0, 1 or 2 and
$R^7$ is a hydrogen atom, a fluorine, chlorine, bromine or iodine atom, an alkyl group having 1–10 carbon atoms, an aryl group having 6–10 carbon atoms, an aralkyl or alkylaryl radical each having 7–10 carbon atoms or is a radical —OR$^5$, where R$^5$ has the meaning indicated above, or is a radical —OCOR$^5$, where R$^5$ has the meaning indicated above, or is a radical —CH$_2$OR$^5$, where R$^5$ has the meaning indicated above, or is a radical —C≡CCH$_2$OH, or R$^3$ and R$^4$ together form an arbitrarily substituted five- or six-membered ring having at least one carbon atom and 0–4 heteroatoms from the group consisting of oxygen, sulfur, selenium, tellurium, nitrogen, phosphorus, silicon or germanium.

Preferred compounds are those where R$^1$ is an alkyl radical having 1–6 carbon atoms. Preferred compounds are also those in which R$^2$ is a methyl or ethyl group. It is furthermore preferred that R$^3$ is a hydroxyl group or an O-alkyl group having 1–6 carbon atoms.

Particularly preferred compounds are those in which R$^4$ is a radical —OR$^5$ or —OCOR$^5$, where R$^5$ is an alkyl radical having 1–6 carbon atoms.

It is furthermore preferred according to the invention that R$^4$ is a radical —(CH$_2$)$_m$—CH=CH(CH$_2$)$_p$—R$^6$, where m=1 and p=1 and R$^6$ is an alkyl radical having 1–6 carbon atoms or a group —OR$^5$ or —OCOR$^5$, where R$^5$ is a hydrogen atom or an alkyl group having 1–6 carbon atoms.

Preferred compounds according to the invention are moreover those in which R$^4$ is a radical —(CH$_2$)$_m$—CH=CH(CH$_2$)$_p$—R$^6$, where m=0 and p=1 and R$^6$ is a group —OR$^5$ or —OCOR$^5$, where R$^5$ is a hydrogen atom or an alkyl group having 1–6 carbon atoms.

Particularly preferred compounds are also those in which R$^4$ is a radical —(CH$_2$)$_o$CH≡CR$^7$, where o=1 and R$^7$ is an alkyl group having 1–6 carbon atoms or a radical —OCOR$^5$, or is a radical —CH$_2$OR$^5$, where R$^5$ is an alkyl radical having 1–6 carbon atoms or a hydrogen atom.

Compounds according to the invention are moreover preferred in which R$^4$ is a radical —(CH$_2$)$_n$CH$_2$Y, where n=0 or 1, Y is an F, Cl, Br or iodine atom, a cyano, amino, azido or thiocyano group, or is a radical —OR$^6$ or —SR$^6$, —(CO)SR$^6$ or —(CO)OR$^6$, where R$^6$ is a hydrogen atom or an alkyl group having 1–10 carbon atoms.

Preferred compounds according to the invention are furthermore characterized in that R$^3$ and R$^4$ together form an arbitrarily substituted five- or six-membered ring having at least one carbon atom and 0–4 heteroatoms, where the heteroatoms originate from the group consisting of oxygen, sulfur and nitrogen.

Particularly preferred compounds here are those where a five-membered ring is formed which contains 1 or 2 heteroatoms.

Very particularly preferred compounds according to the invention are those where the ring is a heterocycle from the group consisting of oxazolidinone, oxazolinone, thiazolidinone, thiazolinone, imidazolidinone, imidazolinone, 1,3-dioxolanone, 1,3-dioxolenone, 1,3-oxathiolanone, 1,3-oxathiolenone, pyrrolidinone, pyrrolinone, oxazolidinethione, oxazolinethione, thiazolidinethione, thiazolinethione, imidazolidinethione, imidazolinethione, dioxolanethione, pyrrolidinethione and pyrrolinethione.

Even more preferred here are compounds where the five-membered ring is an oxazolidin-2-one or an oxazolidine-2-thione.

Those most preferred are:

4-[17β-methoxy-17α-(methoxymethyl)-3-oxoestra-4,9-dien-11β-yl]benzaldehyde 1-(E)[O-(methylthio)carbonyl]oxime, 4-[17β-hydroxy-17α-(methoxymethyl)-3-oxoestra-4,9-dien-11β-yl]benzaldehyde 1-(E)[O-(methylthio)carbonyl]oxime, 4-[17β-methoxy-17α-(methoxymethyl)-3-oxoestra-4,9-dien-11β-yl]benzaldehyde 1-(E)[O-(ethylthio)carbonyl]oxime, 4-[17β-methoxy-17α-(methoxymethyl)-3-oxoestra-4,9-dien-11β-yl]benzaldehyde 1-(Z)[O-(ethylthio)carbonyl]oxime, 4-[17β-methoxy-17α-(ethoxymethyl)-3-oxoestra-4,9-dien-11β-yl]benzaldehyde 1-(E)[O-(ethylthio)carbonyl]oxime, 4-[17β-hydroxy-17α-(methoxymethyl)-3-oxoestra-4,9-dien-11β-yl]benzaldehyde 1-(E)[O-(n-propylthio)-carbonyl]oxime, 4-[17β-methoxy-17α-(n-propoxymethyl)-3-oxoestra-4,9-dien-11β-yl]benzaldehyde 1-(E)[O-(methylthio)carbonyl]oxime, 4-[17β-hydroxy-17α-(i-propoxymethyl)-3-oxoestra-4,9-dien-11β-yl]benzaldehyde 1-(E)[O-(ethylthio)carbonyl]oxime, 4-[17β-hydroxy-17α-(methoxymethyl)-3-oxoestra-4,9-dien-11β-yl]benzaldehyde 1-(E)[O-(ethylthio)carbonyl]oxime, 4-[17β-hydroxy-17α-Z-(3-hydroxypropenyl)-3-oxoestra-4,9-dien-11β-yl]benzaldehyde 1-(E)[O-(methylthio)-carbonyl]oxime, 4-[17β-hydroxy-17α-E-(3-hydroxypropenyl)-3-oxoestra-4,9-dien-11β-yl]benzaldehyde 1-(E)[O-(methylthio)-carbonyl]oxime, 4-[17β-methoxy-17α-(3-hydroxy-1-propinyl)-3-oxoestra-4,9-dien-11β-yl]benzaldehyde 1-(E)[O-(ethylthio)-carbonyl]oxime, 4-[17β-hydroxy-17α-(azidomethyl)-3-oxoestra-4,9-dien-11β-yl]benzaldehyde 1-(E)[O-(methylthio)carbonyl]oxime, 4-[17β-hydroxy-17α-(chloromethyl)-3-oxoestra-4,9-dien-11β-yl]benzaldehyde 1-(E)[O-(ethylthio)carbonyl]oxime, 4-[17β-ethoxy-17α-(chloromethyl)-3-oxoestra-4,9-dien-11β-yl]benzaldehyde 1-(E)[O-(methylthio)carbonyl]oxime, 4-[17β-hydroxy-17α-(cyanomethyl)-3-oxoestra-4,9-dien-11β-yl]benzaldehyde 1-(E)[O-(ethylthio)carbonyl]oxime, 4-[17β-hydroxy-17α-(ethylthiomethyl)-3-oxoestra-4,9-dien-11β-yl]benzaldehyde 1-(E)[O-(ethylthio)carbonyl]-oxime, 4-[17β-hydroxy-17α-(ethylthiomethyl)-3-oxoestra-4,9-dien-11β-yl]benzaldehyde 1-(E)[O-(methylthio)-carbonyl]oxime, 4-[17β-ethoxy-17α-(methylthiomethyl)-3-oxoestra-4,9-dien-11β-yl]benzaldehyde 1-(E)[O-(ethylthio)carbonyl]-oxime, 4-[17β-hydroxy-17α-[(ethylthiocarbonyl)methyl)-3-oxoestra-4,9-dien-11β-yl]benzaldehyde 1-(E)[O-(ethylthio)carbonyl]oxime, 4-[17β-hydroxy-17α-(aminomethyl)-3-oxoestra-4,9-dien-11β-yl]benzaldehyde 1-(E)[O-(ethylthio)carbonyl]oxime and (17R)-4-{3-oxoestra-4,9-dien-17-spiro-5'-oxazolidin-2'-on-11β-yl}benzaldehyde 1-(E)-[O-(ethylthio)-carbonyl]oxime.

The present invention further relates to a process for the preparation of the compounds of the general formula 1 [sic] according to the invention.

The process according to the invention for the preparation of S-substituted 11β-benzaldoxime estra-4,9-dien carbonic acid thioesters of the general formula I,

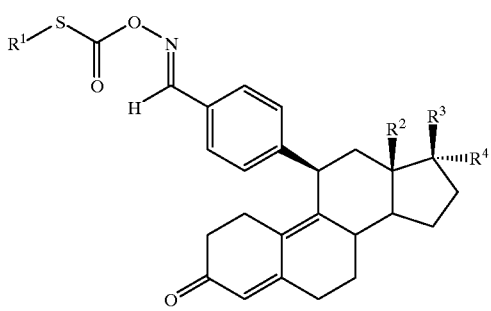

(I)

in which $R^2$, $R^3$ and $R^4$ have the meaning indicated above, is characterized in that, in a manner known per se, a compound of the general formula II,

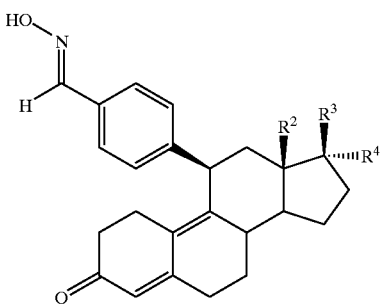

(II)

in which $R^2$, $R^3$ and $R^4$ have the same meaning as $R^2$, $R^3$ and $R^4$ in the formula I, is reacted by treatment with a formic acid derivative of the formula III

Nuc-(CO)—SR¹ (III)

in which

R¹ has the abovementioned meaning and Nuc is a nucleophile, in a solvent and converted into a compound of the general formula I.

A process is preferred here where the solvent employed is a tertiary amine and the reaction is carried out at a temperature between 20° C. and 80° C.

A process is particularly preferred in which the reaction is carried out using chloroformic avid thioesters in pyridine or triethylamine at a temperature between 20° C. and 40° C.

The starting compounds of the general formula II are prepared, if not stated otherwise, by the procedures of the specifications EP-A-0 648 778 or EP-A-0 648 779.

The pharmaceutically acceptable salt is prepared into the I [sic] known manner. Customary physiologically tolerable inorganic and organic acids are, for example, hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Other utilizable acids are described, for example, in Fortschritte der Arzneintmittelforschung, Vol. 10, pages 224–225, Birkhäuser Verlag, Basle and Stuttgart, 1966, and Journal of Pharmaceutical Sciences, Vol. 66, pages 1–5 (1977).

As a rule, the acid addition salts are obtained in a manner known per se by mixing the free base or its solutions with the corresponding acid or its solutions in an organic solvent, for example a lower alcohol such as methanol, ethanol, n-propanol or isopropanol or a lower ketone such as acetone, methyl ethyl ketone or methyl isobutyl ketone or an ether such as diethyl ether, tetrahydrofuran or dioxane. For better crystal deposition, mixtures of the solvents mentioned can also be used. Physiologically tolerable aqueous solutions of acid addition salts of the compound of the formula I can moreover be prepared in an aqueous acid solution.

The acid addition salts of the compounds of the general formula I can be converted into the free base in a manner known per se, e.g. using alkalis or ion exchangers. Further salts can be obtained from the free base by reaction with inorganic or organic acids, in particular those which are suitable for the formation of therapeutically utilizable salts. These or alternatively other salts of the novel compound, such as, for example, the picrate, can also be used for the purification of the free base by converting the free base into a salt, separating this off and in turn liberating the base from the salt.

A further subject of the present invention is pharmaceutical compositions characterized in that they contain at least one compound of the general formula I.

The present invention also relates to medicaments for oral, rectal, subcutaneous, intravenous or intramuscular administration, which together with the customary vehicles and diluents contain at least one compound of the general formula I as active compound.

The medicaments of the invention are prepared in a suitable dose and in a manner known per se using the customary solid or liquid vehicles and/or diluents and the customarily used pharmaceutical excipients according to the desired type of administration. The preferred preparations exist in an administration form which is suitable for oral administration. Such administration forms are, for example, tablets, film-coated tablets, sugar-coated tablets, capsules, pills, powders, solutions or suspensions or depot forms.

Of course, parenteral preparations such as injection solutions are also suitable. Suppositories, for example, may furthermore also be mentioned as preparations.

Suitable tablets can be obtained, for example, by mixing the active compound with known excipients, for example dextrose, sugar, sorbitol, mannitol, polyvinyl-pyrrolidone, disintegrants such as cornstarch or alginic acid, binders such as starch or gelatin, lubricants such as magnesium stearate or talc and/or agents which can achieve a depot effect, such as carboxylpolymethylene, carboxymethylcellulose, cellulose acetate phthalate or polyvinyl acetate. The tablets can also consists of a number of layers.

Accordingly, sugar-coated tablets can be produced by coating cores prepared analogously to the tablets with agents customarily used in sugar-coated tablet coatings, for example polyvinylpyrrolidone or shellac, gum arabic, talc, titanium dioxide or sugar. The sugar-coated shells can in this case also consist of a number of layers, where, for example, the excipients mentioned above in the case of the tablets can be used.

The solutions or suspensions containing the active compound according to the invention can be treated to improve the flavor with substances such as saccharin, cyclamate or sugar and/or with aromatic substances, such as vanillin or orange extract. They can furthermore be mixed with suspension aids such as sodium carboxymethylcellulose or preservatives such as p-hydroxybenzoic acid.

Capsules can be prepared by mixing the medicament with carriers such as lactose or sorbitol, which are then incorporated into the capsules.

Suppositories are prepared, for example, by mixing the active compound with suitable excipients such as neutral fats or polyethylene glycols or its [sic] derivatives.

The compounds of the general formula I according to the invention are bound to the progesterone receptor (cf. Table 1) and in comparison to RU 486 have a markedly reduced antiglucocorticoidal action, demonstrated by the decreased glucocorticoid receptor binding in vitro (cf. Table 1).

TABLE 1

Receptor binding of S-substituted 11β-benzaldoxime estra-4,9-dienecarbonic acid thioesters

| Compound according to example | Relative molar binding affinity RBA (%) to the progesterone receptor Progesterone = 100% | Relative molar binding affinity RBA (%) to the glucocorticoid receptor Dexamethasone = 100% |
|---|---|---|
| 1 (J 1241) | 159 | 49 |
| 2 (J 1247) | 185 | 52 |
| 3 (J 1042) | 164 | 42 |
| 4 (J 1234) | 44 | 53 |
| 5 (J 1240) | 77 | 20 |
| 6 (J 1245) | 64 | 22 |
| 7 (J 1230) | 42 | 2 |
| 8 (J 1244) | 74 | 32 |
| For comparison: | | |
| RU 486 (mifepristone) | 506 | 685 |
| J 867 | 302 | 77 |
| ZK 98299 (onapristone) | 22 | 39 |

J 867 = 11β-[4-(hydroximinomethyl)phenyl]-17β-methoxy-17α-methoxymethyl-estra-4,9-dien-3-one (EP-A-0 648 778 and EP-A-0 648 779)

J 867=11β-[4-(hydroximinomethyl)phenyl]-17β-methoxy-17α-methoxymethyl-estra-4,9-dien-3-one (EP-A-0 648 778 and EP-A-0 648 779)

TABLE 2

Early abortive action in the rat after subcutaneous administration from the 5th–7th day of pregnancy (Administration of 0.2 ml/(animal × day) in benzoyl benzoate/castor oil (1 + 4 v/v)

| Compound according to example | Dose (mg/(animal × day)) | Complete inhibition of pregnancy* N#/N | % |
|---|---|---|---|
| Vehicle | | 0/6 | 0 |
| 2 (J 1247) | 3 | 0/4 | 0 |
| 3 (J 1042) | 10 | 1/5 | 20 |
| | 3 | 0/5 | 0 |
| | 1 | 0/5 | 0 |

TABLE 2-continued

Early abortive action in the rat after subcutaneous administration from the 5th–7th day of pregnancy (Administration of 0.2 ml/(animal × day) in benzoyl benzoate/castor oil (1 + 4 v/v)

| Compound according to example | Dose (mg/(animal × day)) | Complete inhibition of pregnancy* N#/N | % |
|---|---|---|---|
| 7 (J 1230) | 3 | 0/5 | 0 |
| | 1 | 0/5 | 0 |
| RU 486 (Comparison) | 3 | 5/5 | 100 |
| | 1 | 1/5 | 20 |
| | 0.3 | 0/5 | 0 |
| J 867 (Comparison) | 3 | 5/5 | 100 |
| | 1 | 5/5 | 100 |
| | 0.3 | 0/5 | 0 |

*empty uteri
N number of mated females
N# number of non-gravid females

It was surprisingly found that substances according to the invention which had a very high affinity for the progesterone receptor (see Table 1) were not able or only able at very high doses to interfere with early pregnancy in rats. The substances according to the invention (such as, for example, J 1042) proved incapable even at very high doses of interfering with the pregnancy of guinea pigs (see Table 3).

TABLE 3

Abortive action in the guinea pig oh [sic] subcutaneous administration on the 43rd–44th day of pregnancy

| Substance according to example | Dose mg/animal/day | Complete inhibition of pregnancy N#/N | % |
|---|---|---|---|
| 3 (J 1042) | 10 | 0/7 | 0 |
| | 30 | 0/7 | 0 |
| | 100 | 0/7 | 0 |

N number of mated females
N# number of non-gravid females

In spite of high receptor affinity, the compounds according to the invention do not result in any inhibition of luteolysis. It is surprising, then, that the compounds of the formula I have antiovulatory and progesterone-analogous activity in the guinea pig. Other than with Onapristone, which induces proliferation and keratinization of the vaginal epithelium in the guinea pig in cycle in spite of high progesterone levels, among the compounds according to the invention (in spite of low progesterone levels in the blood) a complete inhibition of the proliferation of this epithelium and mucification is seen as an expression of progesterone dominance. In this structure, the effect of the substances according to the invention corresponds to that of additionally tested gestagens (progesterone or levonorgestrel).

With respect to other parameters in the guinea pig, the compounds or the formula I according to the invention can be delimited both against "pure" antagonists of type I (Onapristone) and against agonists (progesterone). Onapristone leads to very low prostaglandin levels in the blood, progesterone and levonorgestrel, on the other hand, to an increased and prolonged uterine secretion of $PGF_{2\alpha}$, reflected by raised prostaglandin F metabolite levels (PGMF [sic] levels) in the blood. PGFM is the long-lived main metabolite of the $PGF_{2\alpha}$ formed by the endometrium, The compounds according to the invention lead to lowered PGFM levels in comparison to control animals in cycle in the luteolysis phase and in comparison to animals treated with gestagen. The PGFM levels are not as low, however, as in animals treated with onapristone.

In rabbits, the substances according to the invention have transformatory activity in the McPhail test and, surprisingly, antitransformatory activity in the same test in combination with progesterone.

Experimental investigations on animals show that the progesterone antagonists according to the invention have such strong partial agonistic actions on the progesterone receptor that abortive effects no longer manifest themselves. Surprisingly, therapy-relevant properties such as, for example, the inhibition of uterine prostaglandin secretion, the inhibition of proliferative processes in tissues of the genital tract and antiovulatory properties, however, are furthermore found.

For the type of active compound described here, the designation ∎mesoprogestin" is proposed, as the designation antigestagen as defined also implies abortive properties which cannot be demonstrated with the compounds according to the invention in animal experiments.

The compounds according to the invention are high-affinity, highly selective modulators of the steroid receptors. In particular, they are agonists or antagonists of the progesterone and androgen receptors.

A further subject of the present invention is therefore the use of the compounds of the general formula I according to the invention for the treatment of endometriosis, uterus myomatosus, dysmenorrhea and premenstrual syndrome, for the induction of reversible amenorrhea without estrogen deficit and for menopausal substitution therapy (Hormone Replacement Therapy HRT) if appropriate in combination with estrogens. The use for the production of contraceptives is also according to the invention.

The compounds of the general formula I according to the invention are also utilizable, according to the invention, in the following indications, such as dysfunctional uterine hemorrhages, herorrhagia, fertility control and fertility modulation, myoma, leiomyoma, osteoporosis, acne, tumors such as breast tumors, endometrial tumors, ovarian tumors, endometriosis, prostate hyperplasia, prostate tumors, hormone-related alopecia and androgenic conditions and defunctionalization symptoms.

EXAMPLES

The Following examples illustrate the Invention:
General procedure for the synthesis of the S-substituted 11β-benzaldoxime estra4,9-diene derivatives 3 mmol of the appropriate S-alkyl(aryl) chloroformate are added to (2 mmol) of 4-[17β-substituted-17α-substituted-3-oxoestra-4,9-dien-11β-yl]benzaldehyde (E or Z)oxime in 10 ml of pyridine. The mixture is stirred at room temperature until conversion is complete, poured into water and the deposited precipitate is filtered off with suction, washed with water and dried. For purification, the crude product is chromatographed and/or recrystallized.

Example 1

4-[17β-Methoxy-17α-(methoxymethyl)-3-oxoestra-4,9-dien-11β-yl]benzaldehyde 1-(E)-[O-(methylthio)carbonyl]oxime Yield; 71% of theory M.p. 134–137° C. (acetone/methyl tert-butyl ether); $\alpha_D$=+184° (CHCl$_3$); IR in KBr [cm$^{-1}$]: 1657 (C=C—C=C—C=O); 1740 (—OC=OSCH$_3$); UV [MeOH]: $\lambda_{max}$ 273 nm; ε=24,505, log ε=4.39, $\lambda_{max}$=289 nm, ε=22,690, log ε=4.36. $^1$H-NMR: [CDCl$_3$; TMS] (δ, ppm): 0.52 (s, 3H, H-18); 2.40 (s, 3H, SCH$_3$); 3.25 (s, 3H, OCH$_3$); 3.40 (s, 3H, OCH$_3$); 3.42 and 3.57 (2d, 2H, J=10.5 Hz, 17α—CH$_2$OCH$_3$); 4.41 (d, 1H, J=6.9 Hz, H-11α); 5.78 (s, 1H, H-4); 7.29 (d, 2H, J=4.5 Hz, H-2'); 7.61 (d, 2H, J=7.8 Hz, H-3'); 8.32 (s, 1H CH=N—OC=OSCH$_3$)

Example 2

4-[17β-Hydroxy-17α-(methoxymethyl)-3-oxoestra-4,9-dien-11β-yl]benzaldehyde 1-(E)-[O-(methylthio)carbonyl]oxime Yield: 68% of theory M.p. 186–189° C. (acetone); $\alpha_D$=+230° (CHCl$_3$); IR in KBr [cm$^{-1}$]: 1602, 1652 (R—CO—R, Ph, >C=N); 1729 (—S—CO—O); UV [MeOH]: $\lambda_{max}$ 274 nm; ε=30,780, log ε=4.49, $\lambda_{max}$=289 nm, ε=28,560, log ε=4.55. $^1$H-NMR: [CDCl$_3$; TMS] (δ, ppm): 0.52 (s, 3H, H-18); 2.40 (s, 3H, —SCH$_3$); 3.21 (d, 1H, J=8.8 Hz, —CH$_2$—O—); 3.41 (s, 3H, —O—CH$_3$); 3.56 (d, 1H, J=8.8 Hz, —CH$_2$—O—); 4.42 (d, 1H, J=7.1 Hz, H-11); 5.79 (s, 1H, H-4); 7.28 (d, 2H, J=8.1 Hz, H-3'); 7.62 (d, 2H, J=8.1 Hz, H-2'); 8.32 (s, 1H, —HC=N)

Example 3

4-[17β-Methoxy-17α-(methoxymethyl)-3-oxoestra-4,9-dien-11β-yl]benzaldehyde 1-(E)-[O-(ethylthio)carbonyl]oxime Yield: 70% of theory M.p. 148–155° C. (acetone/hexane); $\alpha_D$=+235° (CHCl$_3$); IR in KBr [cm$^{-1}$: 1606 (phenyl), 1653 (C=C—C=C—C=O); 1745 (—OC=OSEt), UV [MeOH]: $\lambda_{max}$ 274 nm; ε=31,085, log ε=4.49, $\lambda_{max}$=298 nm, ε=28,280, log ε=4.45. $^1$H-NMR: [CDCl$_3$; TMS] (δ, ppm): 0.52 (s, 3H, H-18); 1.37 (t, 3H, J=7.5 Hz, SCH$_2$CH$_3$); 2.95 (q, 2H, J=4.5 and 15 Hz, SCH$_2$CH$_3$); 3.25 (s, 3H, OCH$_3$); 3.41 (s, 3H, OCH$_3$); 3.42 and 3.57 (2d, 2H, J=10.5 Hz and 10.8 Hz, CH$_2$O); 4.41 (d, 1H, J=7.2 Hz, H-11α); 5.79 (s, 1H, H-4); 7.27 (d, 2H, J=8.4 Hz, H-2'); 7.61 (d, 2H, J=8.4 Hz, H-3'); 7.54 (s, 1H —OH); 8.31 (s, 1H, CH=NOCOSEt)

Example 4

4-[17β-Hydroxy-17α-(methoxymethyl)-3-oxoestra-4,9-dien-11β-yl]benzaldehyde 1-(E)-[O-(ethylthio)carbonyl]oxime Yield 74% of theory M.p. 176–180° C. (dichlorormethane/ethyl acetate); $\alpha_D$=+226° (CHCl$_3$); IR in KBr [cm$^{-1}$]: 1600, 1653 (R—CO—R, Ph, >C=N—) 1729, (—S—CO—O—C=O); UV [MeOH]: $\lambda_{max}$ 274 nm; ε=31,140, log ε=4.59, $\lambda_{max}$=289 nm, ε=28,720, log ε=4.46. $^1$H-NMR; [CDCl$_3$; TMS] (δ, ppm): 0.52 (s, 3H, H-18); 1.36 (t, 3H, J=7.2 Hz, —CH$_2$CH$_3$); 2.73 (dt, 2H, J=1.5, 5.3 Hz, H-7); 2.95 (q, 2H, J=7.2 Hz, —CH$_2$CH$_3$); 3.21 (d, 1H, J=9.2 Hz, —CH$_2$—O—); 3.42 (s, 3H, —O—CH$_3$); 3.56 (d, 1H, J=9.2 Hz, —CH$_2$—O—); 4.41 (d, 1H, J=6.7 Hz, H-11); 5.79 (s, 1H, H-4); 7.27 (d, 2H, J=8.2 Hz, H-3'); 7.62 (d, 2H, J=8.2 Hz, H-2'); 8.32 (s, 1H, —HC=N)

Example 5

4-[17β-Hydroxy-17α-(azidomethyl)-3-oxoestra-4,9-dien-11β-yl]benzaldehyde-1-(E)-[O-(ethylthio)carbonyl]oxime Yield: 64% of theory M.p. 168–171° C. (acetone); $\alpha_D$=+197° (CHCl$_3$); IR in KBr [cm$^{-1}$]: 1658 (C=C—C=C—

C=O); 1693, 1715 (—OC=OSEt) 2094 (N$_3$), UV [MeOH]: $\lambda_{max}$ 274 nm; $\epsilon$=33,150, log $\epsilon$=4.59, $\lambda_{max}$=288 nm, $\epsilon$=28,140, log $\epsilon$=4.45. $^1$H-NMR: [CDCl$_3$; TMS] ($\delta$, ppm): 0.54 (s, 3H, H-18) 1.37 (t, 3H, J=7.2 Hz, SCH$_2$CH$_3$); 1.61 (s, 1H, OH); 2.95 (q, 2H, J=4.5 and 14.7 Hz, CH$_2$CH$_3$); 3.30 and 3.59 (2d, 2H, J=12 Hz, 17$\alpha$—CH$_2$N$_3$); 4.45 (d, 1H, J=6.9 Hz, H-11$\alpha$); 5.80 (s, 1H, H-4); 7.29 (d, 2H, J=8.4 Hz, H-2'); 7.64 (d, 2H, J=8.4 Hz, H-3'); 8.32 (s, 1H, CH=N—OC=OSC$_2$H$_5$)

Preparation of the starting compound
Stage A 1 g of 4-[3,3-dimethoxy-5$\alpha$-hydroxy-17(S)-spiroepoxyestr-9-en-11$\beta$-yl]benzaldehyde 1-ethylene ketal are [sic] suspended in 50 ml of ethylene glycol and the mixture is stirred at 100° C. for 2.5 h with 1 g of sodium azide. The cooled solution is stirred into water, and the precipitate is filtered off with suction, washed until neutral and dried. 870 mg of 4-[17$\alpha$-azidomethyl-3,3-dimethoxy-5$\alpha$,17$\beta$-dihydroxyestr-9-en-11$\beta$-yl]benzaldehyde 1-ethylene ketal are obtained as a pale brown foam, which is employed directly in the next stage.

$^1$H-NMR: [CDCl$_3$; TMS]: 0.47 (s, 3H, H-18); 1.87 (s, 1H, OH); 3.21 and 3.23 (2s, each 3H, OCH$_3$); 3.22 and 3.54 (2d, 2H, J=10.8 Hz, CH$_2$N$_3$); 4.0–4.16 (2m, 4H, ethylene ketal); 4.29 ((d, 1H, J=7.2 Hz, H-11$\alpha$); 4.68 (s, 1H, OH;); 5.76 (s, 1H, CH-ketal); 7.23 (d, 2H, J=8.4 Hz, H-2'); 7.38 (d, 2H, J=8.4 Hz, H-3').

Stage B 650 mg of 4-[17$\alpha$-azidomethyl-3,3-dimethoxy-5$\alpha$, 17$\beta$-dihydroxyestr-9-en-11$\beta$-yl]benzaldehyde 1-ethylene ketal are reacted at room temperature with 155 mg of p-toluenesulfonic acid in 12 ml of acetone and 1.2 ml of water. After 2 h, the mixture is neutralized with aqueous ammonia, a precipitate depositing which is filtered off with suction and dried. The recrystallization of 4-[17$\alpha$-azidomethyl-17$\beta$-hydroxy-3-oxoestra-4,9-dien-11$\beta$-yl] benzaldehyde is carried out from acetone.

M.p. 197–205° C. (acetone); $\alpha_D$=+156° (CHCl$_3$); IR in KBr [cm$^{-1}$]: 1648 (C=C—C=C—C=O); 1712 (CHO), 2100 (N$_3$); UV [MeOH]: $\lambda_{max}$ 203 nm; $\epsilon$=21,143, log $\epsilon$=4.32, $\lambda_{max}$=263 nm, $\epsilon$=8,338, log $\epsilon$=4.26, $\lambda_{max}$ 299 nm, $\epsilon$=20,712, log $\epsilon$=4.32; $^1$H-NMR: [CDCl$_3$; TMS] ($\delta$, ppm): 0.53 (s, 3H, H-18); 2.04 (s, 1H, OH); 3.31 and 3.60 (2d, 2H, J=12.3 Hz, 17$\alpha$—CH$_2$N$_3$); 4.48 (d, 1H, J=7.2 Hz, H-11$\alpha$); 5.81 (s, 1H, H-4); 7.37 (d, 2H, J=8.4 Hz, H-2'); 7.82 (d, 2H, J=8.4 Hz, H-3'); 9.98 (s, 1H, CHO).

Stage C 495 mg of 4-[17$\alpha$-azidomethyl-17$\beta$-hydroxyoxoestra-4, 9-dien-11$\beta$-yl]benzaldehyde are reacted at room temperature in the course of 3 h in 5 ml of pyridine an 80 mg of hydroxylamine hydrochloride. The mixture is poured into ice water and the colorless precipitate is filtered off with suction, dried and purified by chromatography. 380 mg of 4-[17$\alpha$-azidomethyl- 17$\beta$-hydroxy-3-oxoestra-4,9-dien-11$\beta$-yl]benzaldehyde (E)-oxime are obtained.

M.p. 145–151 and 193–200° C. (methyl tert-butyl ether); $\alpha_D$=+212° (CHCl$_3$); IR in KBr [cm$^{-1}$]: 1643, 1657 (C=C—C=C—C=O); 2099 (N$_3$); UV [MeOH]: $\lambda_{max}$ 265 nm; $\epsilon$=21,765, log $\epsilon$=4.34, $\lambda_{max}$=299 nm, $\epsilon$=22,520, log $\epsilon$=4.35; $^1$H-NMR: [DMSO; TMS] ($\delta$, ppm): 0.43 (s, 3H, H-18); 2.04 (s, 1H, OH); 3.09 and 3.40 (2d, 2H, J=12.0 Hz, 17$\alpha$—CH$_2$N$_3$); 4.40 (d, 1H, J=6.2 Hz, H-11$\alpha$); 4.74 (s, 1H, OH); 5.68 (s, 1H, H-4); 7.24 (d, 2H, J=8.1 Hz, H-2); and 7.51 (d, 2H, J=8.1 Hz, H-3'); 8.10 (s, 1H, CH=NOH); 11.16 (2, 1H, OH).

Example 6

4-[17$\beta$-Hydroxy-17$\alpha$-(chloromethyl)-3-oxoestra-4, 9-dien-11$\beta$-yl]benzaldehyde 1-(E)-[O-(ethylthio) carbonyl]oxime M.p. 164–169° C. (acetone/methyl tert-butyl ether); $\alpha_D$=+222° (CHCl$_3$); IR in KBr [cm$^{-1}$]: 1595 (phenyl), 1643 (C=C—C=C—C=O), 1740 (—OC=OSEt); UV [MeOH]: $\lambda_{max}$ 273 nm; $\epsilon$=30,950, log $\epsilon$=4.49, $\lambda_{max}$=288 nm, $\epsilon$=28,140, log $\epsilon$=4.45. $^1$H-NMR: [CDCl$_3$; TMS] 0.59 (s, 3H, H-18); 1.37 (t, 3H, J=7.5 Hz, SCH$_2$CH$_3$); 2.95 (q, 2H, J=4.5 and 15 Hz, SCH$_2$CH$_3$); 3.65, 3.84 (2d, 2H, J=10.8 Hz and 11.1 Hz, CH$_2$O); 4.43 (d, 1H, J=7.2 Hz, H-11$\alpha$); 5.80 (s, 1H, H-4); 7.27 (d, 2H, J=8.1 Hz, H-2'); 7.64 (d, 2H, J=8.4 Hz, H-3'); 8.32 (s, 1H, CH=NOCOSEt);

Example 7

4-[17$\beta$-Hydroxy-17$\alpha$-(cyanomethyl)-3-oxoestra-4,9-dien-11$\beta$-yl]benzaldehyde 1-(E)-O-(ethylthio) carbonyl]oxime Yield: 75% of theory M.p. 178–181° C. (acetone/methyl tert-butyl ether); $\alpha_D$=+222° (CHCl$_3$); IR in KBr [cm$^{-1}$]: 1595 (R—CO—R, Ph, >C=N—) 1736 (—S—CO—O—); 2247 (—CH$_2$—CN) UV [MeOH]: $\lambda_{max}$ 273 nm; $\epsilon$=31,310, log $\epsilon$=4.50, $\lambda_{max}$=288 nm, $\epsilon$=28,560, log $\epsilon$=4.55. $^1$H-NMR: [CDCl$_3$; TMS]: 0.57 (s, 3H, H-18); 1.36 (t, 3H, J=7.5 Hz, —CH$_2$CH$_3$); 2.95 (q, 2H, J=7.5 Hz, —CH$_2$CH$_3$); 4.48 (d, 1H, J=6.7 Hz, H-11): 5.80 (s, 1H, H-4): 7.27 (d, 2H, J=8.2 Hz, H-3'); 7.64 (d, 2H, J=8.2 Hz, H-2')

Example 8

4-{17$\beta$-Hydroxy-17$\alpha$-[(ethylthiocarbonyloxy) methyl]3-oxoestra-4,9-dien-11$\beta$-yl]benzaldehyde 1-(E)-[O-(ethylthio)carbonyl]oxime Yield: 53% of theory M.p. 152–156° C. (acetone); $\alpha_D$=+166° (CHCl$_3$); IR in KBr [cm$^{-1}$]: 1655 (C=C—C=C—C=O); 1691 (—OC=OSEt); UV [MeOH]: $\lambda_{max}$ 273 nm; $\epsilon$=31,290, log $\epsilon$=4.50, $\lambda_{max}$=288 nm, $\epsilon$=28,490, log $\epsilon$=4.45. $^1$H-NMR: [CDCl$_3$; TMS]: 0.55 (s, 3H, H-18); 1.35 and 1.37 (2t, 2× 3H, CH$_2$CH$_3$); 2.13 (s, 1H, OH); 2.40 (s, 3H, SCH$_3$); 2.87–2.99 (m, 4H, 2× CH$_2$CH$_3$); 4.20 and 4.34 (2d, 2H, J=10.8 Hz, 17$\alpha$—CH$_2$OCH$_3$); 4.43 (d, 1H, J=6.9 Hz, H-11$\alpha$); 5.80 (s, 1H, H-4); 7.27 (d, 2H, J=8.1 Hz, H-2'); 7.64 (d, 2H, J=8.4 Hz, H-3'); 8.32 (s, 1H, CH=N—OC=OSCH$_3$)

Preparation of the starting compound
Stage A 3 g of 4-[3,3-dimethoxy-5$\alpha$-hydroxy-17(S)-spiroepoxyestr-9-en-11$\beta$-yl]benzaldehyde 1-ethylene ketal is [sic] heated at 110° C. for 5 h with 22 ml of 2N NaOH in 65 ml of methylpyrrolidone and then poured into ice water. The mixture is extracted with ethyl acetate, and the organic phase is washed until neutral, dried and evaporated in vacuo.

The dark oil is purified by chromatography. 1.13 g mg [sic] of 4-[3,3-dimethoxy-5$\alpha$,17$\beta$-dihydroxy-17$\alpha$-(hydroxymethyl)estr-9-en-11$\beta$-yl]benzaldehyde 1-ethylene ketal are obtained as a pale yellow foam, which is employed directly in the next stage.

$^1$H-NMR: (CDCl$_3$; TMS]: 0.47 (s, 3H, H-18); 2.04 (s, 1H, OH); 3.21 and 3.22 (2s, each 3H, OCH$_3$); 3.40 and 3.74 (2d, 2H, J=10.8 Hz, CH$_2$OH after HD exchange); 4.0–4.15 (2m, 4H, ethylene ketal); 4.29 (d, 1H, J=7.2 Hz, H-11$\alpha$); 4.67 (s, 1H, OH); 5.76 (s, 1H, CH ketal); 7.23 (d, 2H, J=8.4 Hz, H-2'); 7.37 (d, 2H, J=8.4 Hz, H-3')

Stage B 1.13 g of 4-[3,3-dimethoxy-5$\alpha$,17$\beta$-dihydroxy-17$\alpha$-(hydroxymethyl)estr-9-en-11$\beta$-yl]benzaldehyde 1-ethylene ketal are dissolved in 17 ml of THF and stirred at room temperature for 4 h with 2.0 ml of water and 260 mg of p-toluenesulfonic acid. The mixture is concentrated to half the volume in vacuo and the solution is stirred into ice water. It is extracted 2× with ethyl acetate, and the organic phase is washed until neutral, dried and evaporated in Vacua. The crude product is recrystallized several times from ethyl acetate. 308 mg of 4-[17β-hydroxy-17α-(hydroxymethyl)-3-oxoestra-4,9-dien-11β-yl]benzaldehyde are obtained.

M.p. 211–220° C. (acetic acid); $α_D$=+185° (CHCl$_3$); IR in KBr [cm$^{-1}$]: 1661 (C=C—C=C—C=O); 1693 (CH=O); UV [MeOH]: $λ_{max}$ 264 nm; ε=14,560, log ε=4.16, $λ_{max}$=299 nm, ε=16,180, log ε=4.20.

$^1$H-NMR: [CDCl$_3$; TMS] 0.53 (s, 3H, H-18); 3.4 and 3.8 (2 m, 2H, CH$_2$O, 4.65 d and 4.95 d after TAI addition: J=12.0 Hz); 4.43 (d, 1H, J=7.2 Hz, H-11α); 5.80 (s, 1H, H-4); 7.38 (d, 2H, J=8.1 Hz, H-2'); 7.81 (d, 2H, J=8.4 Hz, H-3'); 9.97 (s, 1H, CH=O).

Stage C 752 mg of 4-17β-hydroxy-17α-(hydroxymethyl)-3-oxoestra-4,9-dien-11β-yl]benzaldehyde are reacted with stirring at room temperature in the course of 40 minutes with 128 mg of hydroxylamine hydrochloride in 8 ml of pyridine under argon. The solution is poured into ice water, and the precipitate is filtered off with suction, washed and dried. 690 mg of 4-[17β-hydroxy-17β-(hydroxymethyl)-3-oxoestra-4,9-dien-11β-yl]benzaldehyde (E)-oxime are obtained.

M.p. 198–204° C. (acetic acid/methyl tert-butyl ether); $α_D$=+237° (MeOH); IR in KBr [cm$^{-1}$]: 1637, 1650, 1657 (C=C—C=C—C=O); UV [MeOH]: $λ_{max}$ 264 nm; ε=20,503, log ε=4.31, $λ_{max}$=299 nm, ε=20,020, log ε=4.30; $^1$H-NMR; [CDCl$_3$; TMS]: 0.53 (s, 3H, H-18); 3.4 and 3.8 (2 m, 2H, CH$_2$O, 4.65 d and 4.95 d after TAI addition: J=12.0 Hz); 4.43 (d, 1H, J=7.2 Hz, H-11α); 5.80 (s, 1H, H-4); 7.38 (d, 2H, J=8.1 Hz, H-2'); 7.81 (d, 2H, J=8.4 Hz, H-3'); 9.97 (s, 1H, CH=O).

Example 9

4-[17β-Hydroxy-17α-(ethylthiomethyl)-3-oxoestra-4,9-dien-11β-yl]benzaldehyde 1-(E)-[O-(ethylthio) carbonyl]-oxime Yield: 73% of theory M.p. 138–1410° C. (acetone/EtOH); $α_D$=+184° (CHCl$_3$); IR in KBr [cm$^{-1}$]: 1602 (phenyl), 1646, 1650 (C=C—C=C—C=O); 1731, 1737 (OC=OSEt); UV [MeOH]: $λ_{max}$ 274 nm; ε=31,420, log ε=4.50, $λ_{max}$=288 nm, ε=28,750, log ε=4.46; $λ_{max}$ 297 nm ε=28,220, log ε=4.45; $^{-1}$H-NMR: [CDCl$_3$; TMS]: 0.55 (s, 3H, H-18); 1.29 (t, 3H, J=7.2 Hz, SCH$_2$CH$_3$); 1.37 (t, 3H, J=7.2 Hz, SCH$_2$CH$_3$); 2.60 (q, 2H; J=7.2 Hz and J=14.7 Hz, SCH$_2$CH$_3$); 2.71 and 2.96 (2d, 2H, J=12.9 Hz, 17α—CH$_2$SC$_2$CH$_3$); 2.85 (s, 1H, OH); 2.95 (m, 2H, SCH$_2$CH$_3$); 4.44 (d, 1H, J=7.2 Hz, H-11α); 5.79 (s, 1H, H-4); 7.27 (d, 2H, J=8.4 Hz, H-2'); 7.63 (d, 2H, J=8.4 Hz, H-3 1'); 8.32 (s, 1H, CH=NOR).

Preparation of the starting compound

Stage A 1.48 g of 4-[3,3-dimethoxy-5α-hydroxy-17(S) spiroepoxyestr-9-en-11β-yl]benzaldehyde 1-ethylene ketal is [sic] heated to 80° C. with stirring with 500 mg of sodium thioethanolate in 15 ml of DMSO. The mixture is poured into ice water, and the solid is filtered off with suction and washed until neutral. After drying, 1.47 g of 4-[3,3-dimethoxy-5α,17β-dihydroxy-17α-(ethylthiomethyl)estr-9-en-11β-yl]benzaldehyde 1-ethylene ketal are obtained as a brown crude product, which is employed directly in the next stage.

Stage B 1.47 g of 4-[3,3-dimethoxy-5α,17β-dihydroxy-17α-(ethylthiomethyl)estr-9-en-11β-yl]benzaldehyde 1-ethylene ketal is [sic] reacted at room temperature in the course of 4 h with 140 mg of p-toluenesulfonic acid in 15 ml of acetone, The mixture is poured into aqueous bicarbonate solution, and the precipitate is faltered off with suction and washed until neutral. The precipitate (1.24 g) is purified by chromatography, 640 mg of 4-[17α-ethylthiomethyl-17β-hydroxy-3-oxoestra-4,9-dien-11β-yl]benzaldehyde are obtained.

M.p. 180–182° C. (acetone); $α_D$=+160° (CHCl$_3$); IR in KBr [cm$^{-1}$]: 1650, 1656 (C=C—C=C—C=O); 1697 (CH=O); UV [MeOH]: $λ_{max}$ 264 nm; ε=20,375, log ε=4.31, $λ_{max}$ =299 nm, ε=22,810, log ε=4.36. $^1$H-NMR: [CDCl$_3$; TMS]: 0.54 (s, 3H, H-18); 1.29 (t, 3H, SCH$_2$CH$_3$); 2.61 (m, 2H, SCH$_2$CH$_3$); 2.88 (s, 1H, OH); 2.71 and 2.95 (2d, 2H, J=12.9 Hz, CH$_2$S); 4.48 (d, 1H, J=7.2 Hz, H-11α); 5.80 (s, 1H, H-4); 7.37 (d, 2H, J=8.1 Hz, H-2'); 7.81 (d, 2H, J=8.4 Hz, H-3'); 9.98 (s, 1H, CH=O).

Stage C 392 mg of 4-[17β-hydroxy-17α-(ethylthiomethyl)-3-oxoestra-4,9-dien-11β-yl]benzaldehyde is [sic] reacted in the course of 3.5 h at room temperature with 61 mg of hydroxylamine hydrochloride in 20 ml of pyridine. The mixture is poured into ice water and the colorless precipitate is filtered off with suction, washed with water until neutral and dried in vacuo. 560 mg of crude product are purified by chromatography and recrystallized from acetone. 335 mg of 4-[17β-hydroxy-17β-ethylthiomethyl-3-oxoestra-4,9-dien-11β-yl]benzaldehyde (E)-oxime are obtained.

M.p. 132–137° C. (acetone); $α_D$=+165° (CHCl$_3$); IR in KBr [cm$^{-1}$]: 1649, 1655 (C=C—C=C—C=O); UV [MeOH]: $λ_{max}$ 264 nm; ε=23,800, log ε=4.38, $λ_{max}$=299 nm, ε=23,045, log ε=4.36; $^1$H-NMR: [CDCl$_3$; TMS]: 0.56 (s, 3H, H-18); 1.29 (t, 3H, J=7.5 Hz, SCH$_2$CH$_3$), 2.61 (m, 2H; SCH$_2$CH$_3$); 2.71 and 2.96 (2d, 2H, J=12.9 Hz, 17α—CH$_2$SC$_2$CH$_3$); 2.90 (s, 1H, OH); 4.42 (d, 1H, J=7.2 Hz, H-11α); 5.79 (s, 1H, H-4); 7.20 (d, 2H, J=8.4 Hz, H-2); 7,49 (d, 2H, J=8.4 Hz, H-3'); 7.93 (s, 1H, NOH); 8.10 (s, 1H CH=N).

Example 10

(17R)-4-{3-Oxoestra-4,9-diene-17-spiro-5'-oxazolidin-2'-on-11β-yl)benzaldehyde 1-(E)-[O (ethylthio)-carbonyl]oxime M.p. 133–138 and 150–158° C. (acetone/ethanol); $α_D$=+193° (CHCl$_3$); IR in KBr [cm$^{-1}$]: 1658 (C=C—C=C—C=O); 1719 (C=O); UV [MeOH]: $λ_{max}$ 273 nm; ε=26,830, log ε=4.43, $λ_{max}$=298 nm, ε=24,240, log ε=4.38; $^1$H-NMR: [CDCl$_3$; TMS]: 0.53 (s, 3H, H-18); 1.37 (t, 3H, J=7.5 Hz, SCH$_2$CH$_3$), 2.95 (q, 95 2H, SCH$_2$CH$_3$); 3.81 (d, 1H, J=11.7 Hz, 17α—CH$_2$S—); 4.43 (d, 1H, J=6.6 Hz, H-11α); 4.52 (d, 1H, J=11.7 Hz, 17α—CH$_2$S—); 4.54 (s, 1H, NH); 5.80 (s, 1H, H-4); 7.28 (d, 2H, J=8.4 Hz, H-2'); 7.63 (d, 4H, J=8.4 Hz, H-3'); 8.32 (s, 1H CH=N).

Preparation of the starting compound

Stage A 1.86 g of 4-[17α-chloromethyl-17β-hydroxy-3-oxoestra-4,9-dien-11β-yl]benzaldehyde are reacted at room temperature in the course of 1 hour with 0.76 ml of trichloroacetyl isocyanate in 50 ml of CH$_2$Cl$_2$. After addition of aqueous NH$_4$Cl solution, the phases are separated. The organic phase is washed until neutral, dried and evaporated in vacuo. 4-[17α-Chloroethyl-17β-(trichloroacetylcarbamoyl)-3-oxoestra-4,9-dien-11β-yl]benzaldehyde is obtained as a foam, which is taken up in methylene chloride. The solution is stirred at room temperature for 5 h together with 10 g of alumina (Woelm super I, basic). The alumina is then filtered off and reextracted with methylene chloride and methanol. The solvent is evaporated and a brawn foam is purified by chromatography on silica gel. 850 mg of (17R)-4-(3-oxoestra-4,9-dien-17-spiro-5'-oxazolidin-2'-on-11β-yl}benzaldehyde are isolated.

M.p. 173° C. decomposition (methyl tert-butyl ether/acetone/hexane); $\alpha_D$=+152° (CHCl$_3$); IR in KBr [cm$^{-1}$]: 1603 (phenyl), 1650, 1682 (C=C—C=C—C=O); 1701, 1721 (C=O); UV [MeOH]; $\lambda_{max}$ 262 nm; $\epsilon$=18,090, log $\epsilon$=4.26, $\lambda_{max}$=297 nm, $\epsilon$=20,760, log $\epsilon$=4.32; $^1$H-NMR: [CDCl$_3$; TMS]: 0.53 (s, 3H, H-18); 3.82 (d, 1H, J=11.7 Hz, 17α—CH$_2$NH—); 4.48 (d, 1H, J=6.9 Hz, H-11α); 4.52 (d, 1H, J=11.7 Hz, 17α—CH$_2$NH—); 4.59 (s, 1H, NH); 5.81 (s, 1H, H-4); 7.39 (d, 2H, J=8.4 Hz, H-2'); 7.82 (d, 4H, J=8.4 Hz, H-3'); 9.98 (s, 1H CH=O); after TAI addition; 0.56 (s, 3H, H-18); 3.90 (d, 1H, J=12.3 Hz, 17α—CH$_2$NH—); 4.37 (d, 1H, J=12.3 Hz, 17α—CH$_2$NH—); 4.52 (d, 1H, J=7.2 Hz, H-11α); 5.83 (s, 1H, H-4); 7.38 (d, 2H, J=8.1 Hz, H-2'); 7.82 (d, 4H, J=8.1 Hz, H-3'); 9.98 (s, 1H, CH=O), 10.45 (broad s, 1H, NCONHC=OCCl$_3$).

Stage B 440 mg of (17R)-4-(3-oxoestra-4,9-dien-17-spiro-5'-oxazolidin-2'-on-11β-yl)benzaldehyde are reacted at room temperature in the course of 4 h with 70 mg of hydroxylamine hydrochloride in 10 ml of pyridine. The precipitate is poured into ice water, filtered off with suction, dried and purified by chromatography. After recrystallization from acetone/methyl tert-butyl ether, 180 mg of (17R)-4-(3-oxoestra-4,9-dien-17-spiro-5'-oxazolidin-2'-on-11β-yl)benzaldehyde 1-(E)-oxime are obtained.

M.p. 181° C. decomposition (methyl tert-butyl ether/acetone); $\alpha_D$=+183° (DMSO); IR in KBr [cm$^{-1}$]: 1614 (phenyl) , 1660, 1694 (C=C—C=C—C=O); 1729 (C=O); UV [MeOH]: $\lambda_{max}$ 264 nm; $\epsilon$=21,930, log $\epsilon$=4.34, $\lambda_{max}$=298 nm, $\epsilon$=21,930, log $\epsilon$=4.34; $^1$H-NMR: [DMSO; TMS]: 0.47 (s, 3H, H-18); 3.97 (d, 1H, J=10.8 Hz, 17α—CH$_2$NH—); 4.46 (d, 1H, J=6.3 Hz, H-11α); 4.58 (d, 1H, J=11.4 Hz, 17α—CH$_2$NH—); 4.59 (s, 1H, NH); 5.69 (s, 1H, H-4); 6.3 and 6.5 (broad s, NH); 7.21 (d, 2H, J=8.1 Hz, H-2'); 7.51 (d, 4H, J=8.4 Hz, H-3'); 8.08 (s, 1H, CH=N); 11.17 (s, 1H, OH).

Example 11

Measurement of the receptor binding affinity

The receptor binding affinity was determined by competitive binding of a specifically binding $^3$H-labeled hormone (tracer) and the compound to be tested to receptors in the cytosol of animal target organs. Receptor saturation and reaction equilibrium were aimed at here. The following incubation conditions were chosen:

Progesterone receptor Uterus cytosol of the estradiol-primed rabbit, stored at –30° C.

Buffer for homogenization and incubation: TED buffer 20 mM tris/HCl, p$_H$ [sic]=7.4; 1 mM ethylenediamine tetracetate, 2 mM dithiothreitol) containing 250 mM sucrose.

Tracer: $^3$H-ORG 2058, 5 nM;

Reference substance: progesterone.

Glucocorticoid receptor: Thymus cytosol of the adrenalectomized rat. Thymi stored at –30° C.

Buffer: TED.

Tracer: $^3$H-dexamethasone, 20 nM.

Reference substance: dexamethasone.

After an incubation of receptor fraction, tracer and competitor for 18 h at 0–4° C., the bound and free steroid were separated by mixing in active carbon/dextran (1%/0.1%), centrifuging off and measuring the receptor-bound $^3$H activity in the supernatant.

The IC$_{50}$ for the reference substance and for the compound to be tested were determined from the measurement in concentration series and the relative molar binding affinity was determined as the quotient of both values (×100%).

Example 12

Inhibition of early pregnancy in the rat

Female rats weighing 180–200 g were mated in the proestrus stage. On detection of sperm in the vaginal region on the next day, this is set as day 1 (d=1) of the pregnancy. The rats are treated with test substance or vehicle using 0.2 ml of benzoyl benzoate/castor oil (1+4 v/v) subcutaneously from day 5 to day 7 (d5–d7); autopsy is carried oust painlessly on day d9. The uterus horns was [sic] dissected and examined for intact or damaged nidation sites. The rate of completely inhibited pregnancies in the individual groups follows from Table 2.

Example 13

Inhibition of late pregnancy in pregnant guinea pigs

Pregnant guinea pigs are treated with test substances from day 43–44. Experimental animals were infected with the test substance in oily solution (0.2–2.0 ml of benzoyl benzoate/castor oil 1+4 v/v) 1× daily on day 43 and 44. Control animals were treated with vehicle. The pregnancy of the animals was monitored until day 50, in particular, the expulsion of fetuses and placentas was observed and recorded.

Example 14

Antiluteolysis test/ovulation inhibition test in the guinea pig in cycle:

This test is based on the fact that progesterone at the end of the cycle stimulates uterine prostaglandin secretion. In the guinea pig, the inhibition of this function leads to a persistence of the corpora lutea (antiluteolysis).

In this test, progesterone receptor antagonists having partial agonistic activity are slightly antiluteolytically active (see RU 486) or not antiluteolyticaily active at all. Progesterone-agonistic activity can likewise be demonstrated in this experiment design, on the one hand by antiovulatory activity, but on the other by demonstration of typical progesterone effects in the genital tract. This test thus allows the therapy-relevant typing of progesterone antagonists as ▪pure" or ▪agonistic" substances.

Guinea pigs are treated with the test substance on day 10 to day 17 of the cycle. The progesterone concentrations in the serum are determined on day 10 before substance treatment and on the following days until autopsy (Elger, W., Neef, G., Beier, S., Fähnrich, M., Crundel, M. et al. in Current Concepts in Fertility Regulation and Reproduction, (eds). Puri, C. P. and Van Look, P. F. H. (1994) 303–328).

Example 15

McPhail test on immature female rabbits:

The endometrium of sexually immature rabbits reacts to gestagens with a typical histological transformation. This is the basis of the McPhail test. This was employed in order to test whether substances to which this invention relates have progesterone-like properties. In addition, the antagonistic partial action of these substances was investigated on simultaneous treatment with a maximally transforming dose off progesterone. The action in the Mcphail test is recorded by the ▪McPhail scores" 1–4, score 4 corresponding to a maximal transformation.

What is claimed is:

1. An S-substituted 11β-benzaldoxime-estra-4,9-diencarbonic acid thioester compound of the formula I:

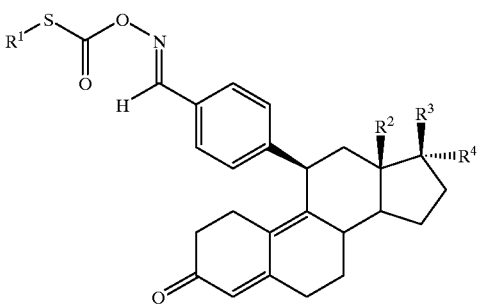

(I)

or a pharmaceutically acceptable salt thereof; wherein
$R^1$ is an alkyl radical having 1 to 10 carbon atoms, an aryl radical having 6 to 10 carbon atoms or an alkylaryl or arylalkyl radical each having 7 to 10 carbon atoms;

$R^2$ is a hydrogen atom or an alkyl radical having 1 to 3 carbon atoms;

$R^3$ is a hydroxyl group, an O-alkyl group having 1 to 10 carbon atoms, an O-aryl group having 6 to 10 carbon atoms, an O-aralkyl group or an O-alkylaryl group, each having 7 to 10 carbon atoms, —OCOR$^5$, —OCONHR$^5$ or —OCOOR$^5$;

$R^4$ is a hydrogen atom, an alkyl group having 1 to 10 carbon atoms, an aryl group having 6 to 10 carbon atoms, an aralkyl or alkylaryl group each having 7 to 10 carbon atoms, —C≡CCH$_2$OH, —(CH$_2$)$_n$CH$_2$Y, —OR$^5$, —OCOR$^6$, —(CH$_2$)$_m$—CH=CH(CH$_2$)$_p$—R$^{6'}$ or —(CH$_2$)$_o$C≡CR$^7$;

wherein n=0, 1 or 2; m=0, 1, 2 or 3; p=0, 1 or 2; and o=0, 1 or 2;

wherein Y is a fluorine atom, a chlorine atom, a bromine atom, an iodine atom, a cyano group, an amino group, an azido group, a thiocyano group, —OR$^6$, —SR$^6$, —(CO)OR$^6$ or —(CO)SR$^6$;

wherein R$^6$ is a hydrogen atom, an alkyl radical having 1 to 10 carbon atoms, an aryl radical having 6 to 10 carbon atoms, an alkylaryl or arylalkyl radical each having 7 to 10 carbon atoms or —COR$^5$;

wherein R$^{6'}$ is a hydrogen atom, an alkyl radical having 1 to 10 carbon atoms, an aryl radical having 6 to 10 carbon atoms, an alkylaryl or arylalkyl radical each having 7 to 10 carbon atoms, —OR$^5$, —OC OR$^5$ or —COR$^5$;

wherein R$^7$ is a hydrogen atom, a fluorine atom, a chlorine atom, a bromine atom, an iodine atom, an alkyl radical having 1 to 10 carbon atoms, an aryl radical having 6 to 10 carbon atoms, an alkylaryl or arylalkyl radical each having 7 to 10 carbon atoms, —OR$^5$, —CH$_2$OR$^5$ or —OCOR$^5$; and wherein R$^5$ is a hydrogen atom, an alkyl group having 1 to 10 carbon atoms, an aryl group having 6 to 10 carbon atoms or an aralkyl or alkylaryl group each having 7 to 10 carbon atoms; or, alternatively, wherein R$^3$ and R$^4$ taken together form an optionally substituted five-member or six-member ring having at least one carbon atom and from 0 to 4 hetero atoms, and each of said hetero atoms is selected from the group consisting of oxygen, sulfur, selenium, tellurium, nitrogen, phosphorus, silicon and germanium.

2. The compound as defined in claim 1, wherein said $R^1$ is an alkyl group having 1 to 6 carbon atoms.

3. The compound as defined in claim 1, wherein said $R^2$ is a methyl or ethyl group.

4. The compound as defined in claim 1, wherein said $R^3$ is said hydroxyl group.

5. The compound as defined in claim 1, wherein said $R^3$ is an O-alkyl radical having 1 to 6 carbon atoms.

6. The compound as defined in claim 1, wherein said $R^4$ is said —OR$^5$ or said —OCOR$^5$ and said R$^5$ is an alkyl radical having 1 to 6 carbon atoms.

7. The compound as defined in claim 1, wherein said $R^4$ is said —(CH$_2$)$_m$—CH=CH(CH$_2$)$_p$—R$^{6'}$, wherein said m is 1 and said p is 1 and wherein said R$^{6'}$ is an alkyl group having 1 to 6 carbon atoms, said —OR$^5$ or said —OCOR$^5$; said R$^5$ is said hydrogen atom or an alkyl radical having 1 to 6 carbon atoms.

8. The compound as defined in claim 1, wherein said $R^4$ is said —(CH$_2$)$_m$—CH=CH(CH$_2$)$_p$—R$^{6'}$, wherein said m is 1 and said p is 1 and wherein said R$^{6'}$ is said —OR$^5$ or said —OCOR$^5$; said R$^5$ is said hydrogen atom or an alkyl radical having 1 to 6 carbon atoms.

9. The compound as defined in claim 1, wherein said $R^4$ is said —(CH$_2$)$_o$C≡CR$^7$; said o is 1; said R$^7$ is an alkyl group having 1 to 6 carbon atoms, said —CH$_2$OR$^5$ or said —OCOR$^5$, said R$^5$ being said hydrogen atom or an alkyl radical having 1 to 6 carbon atoms.

10. The compound as defined in claim 1, wherein said $R^4$ is said —(CH$_2$)$_n$CH$_2$Y, said n is 0 or 1, said Y is said fluorine atom, said chlorine atom, said bromine atom, said iodine atom, said cyano group, said amino group, said azido group, said thiocyano group, said —OR$^6$, said —SR$^6$, said —(CO)OR$^6$ or said —(CO)SR$^6$ with said R$^6$ being said hydrogen atom or said alkyl radical having 1 to 10 carbon atoms.

11. The compound as defined in claim 1, wherein said optionally substituted five-member or six-member ring has said at least one carbon atom and said 0 to 4 hetero atoms and each of said hetero atoms is selected from the group consisting of oxygen, sulfur and nitrogen.

12. The compound as defined in claim 1, said $R^3$ and $R^4$ taken together form said optionally substituted five-member ring having 1 or 2 of said hetero atoms.

13. The compound as defined in claim wherein said optionally substituted five-member ring is an optionally substituted heterocyclic ring and said optionally substituted heterocyclic ring is selected from the group consisting of oxazolidinone, oxazolinone, thiazolidinone, thiazolinone, imidazolidinone, imidazolinone, 1,3-dioxolanone, 1,3-dioxolenone, 1,3-oxathiolanone, 1,3-oxathiolenone, pyrrolidinone, pyrrolinone, oxazolidinethione, oxazolinethione, thiazolidinethione, thiazolinethione, imidazolidinethione, imidazolinethione, dioxolanethione, pyrrolidinethione and pyrrolinethione.

14. The compound as defined in claim 12, wherein said optionally substituted five-member ring is an optionally substituted heterocyclic ring and said optionally substituted heterocyclic ring is an oxazolidin-2-one or an oxazolidin-2-thione.

15. An S-substituted 11β-benzaldoxime-estra-4,9-dien-carbonic acid thioester compound selected from the group consisting of 4-[17β-methoxy-17α-(methoxymethyl)-3-oxoestra-4,9-dien-11β-yl]-benzaldehyde 1-(E)[O-(methylthio)carbonyl]oxime, 4-[17β-hydroxy-17α-(methoxymethyl)-3-oxoestra-4,9-dien-11β-yl]-benzaldehyde 1-(E)[O-(methylthio)carbonyl]oxime, 4-[17β-methoxy-17α-(methoxymethyl)-3-oxoestra-4,9-dien-11β-yl]-benzaldehyde 1-(E)[O-(ethylthio)carbonyl]oxime, 4-[17β-methoxy-17α-(methoxymethyl)-3-oxoestra-4,9-dien-11β-yl]-benzaldehyde 1-(Z)[O-(ethylthio)carbonyl]oxime, 4-[17β-methoxy-17α-(methoxymethyl)-3-oxoestra-4,9-dien-11β-yl]-benzaldehyde 1-(E)[O-(ethylthio)carbonyl)oxime, 4-[17β-hydroxy-17α-(methoxymethyl)-3-oxoestra-4,9-dien-11β-yl]-benzaldehyde 1-(E)[O-(n-propylthio)-carbonyl]oxime, 4-[17β-methoxy-17α-(n-propoxymethyl)-3-oxoestra-4,9-dien-11β-yl]-benzaldehyde 1-(E)[O-(methylthio)carbonyl]oxime, 4-[17β-hydroxy-17α-(i-propoxymethyl)-3-oxoestra-4,9-dien-11β-yl]-benzaldehyde 1-(E)(O-(ethylthio)carbonyl]oxime, 4-[17β-hydroxy-17α-(methoxyethyl)-3-oxoestra-4,9-dien-11β-yl]-benzaldehyde 1-(E)[O-(ethylthio)carbonyl]oxime, 4-[17β-hydroxy-17α-Z-(3-hydroxypropenyl)-3-oxoestra-4,9-dien-11β-yl]-benzaldehyde 1-(E)[O-(methylthio)-carbonyl]oxime, 4-[17β-hydroxy-17α-E-(3-hydroxypropenyl)-3-oxoestra-4,9-dien-11β-yl]-benzaldehyde 1-(E)[O-(methylthio)carbonyl]oxime, 4-[17β-methoxy-17α-(3-hydroxy-1-propinyl)-3-oxoestra-4,9-dien-11β-yl]-benzaldehyde 1-(E)[O-(ethylthio)carbonyl]oxime, 4-[17β-hydroxy-17α-(azidomethyl)-3-oxoestra-4,9-dien-11β-yl]-benzaldehyde 1-(E)-[O-(methylthio)carbonyl]oxime, 4-[17β-hydroxy-17α-(chloromethyl)-3-oxoestra-4,9-dien-11β-yl]-benzaldehyde 1-(E)[O-(ethylthio)carbonyl]oxime, 4-[17β-ethoxy-17α-(chloromethyl)-3-oxoestra-4,9-dien-11β-yl]-benzaldehyde 1-(E)[O-(methylthio)carbonyl)oxime 4-[17β-hydroxy-17α-(cyanomethyl)-3-oxoestra-4,9-dien-11β-yl-benzaldehyde 1-(E)[O-(ethylthio)carbonyl]oxime, 4-[17β-hydroxy-17α-(ethylthiomethyl)-3-oxoestra-4,9-dien-11β-yl]-benzaldehyde 1-(E)[O-(ethylthio)carbonyl]oxime, 4-[17β-hydroxy-17α-(ethylthiomethyl)-3-oxoestra-4,9-dien-11β-yl]-benzaldehyde 1-(E)[O-(methylthio)carbonyl]oxime, 4-[17β-ethoxy-17α-(methylthiomethyl)-3-oxoestra-4,9-dien-11-yl]-benzaldehyde 1-(E)[O-(ethylthio)carbonyl]oxime, 4-[17β-hydroxy-17α-[(ethylthiocarbonyl)methyl-3-oxoestra-4,9-dien-11β-yl]benzaldehyde 1-(E)[O-(ethylthio)carbonyl]oxime, 4-[17β-hydroxy-17α-(aminomethyl)-3-oxoestra-4,9-dien-11β-yl]-benzaldehyde 1-(E)[O-(ethylthio)carbonyl]oxime and (17R)-4-(3-oxoestra-4,9-dien-17-spiro-5'-oxazolidin-2'-on-11β-yl)-benzaldehyde 1-(E)-[O-(ethylthio)-carbonyl]oxime.

16. A process for preparation of an S-substituted 11β-benzaldoxime-estra-4,9-dien-carbonic acid thioester compound of the formula I:

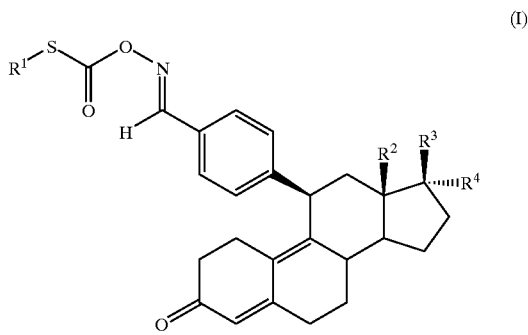

or a pharmaceutically acceptable salt thereof;
wherein
$R^1$ is an alkyl radical having 1 to 10 carbon atoms, an aryl radical having 6 to 10 carbon atoms or an alkylaryl or arylalkyl radical each having 7 to 10 carbon atoms;

$R^2$ is a hydrogen atom or an alkyl radical having 1 to 3 carbon atoms;

$R^3$ is a hydroxyl group, an O-alkyl group having 1 to 10 carbon atoms, an O-aryl group having 6 to 10 carbon atoms, an O-aralkyl group or an O-alkylaryl group, each having 7 to 10 carbon atoms, —OCOR$^5$, —OCONHR$^5$ or —OCOOR$^5$;

$R^4$ is a hydrogen atom, an alkyl group having 1 to 10 carbon atoms, an aryl group having 6 to 10 carbon atoms, an aralkyl or alkylaryl group each having 7 to 10 carbon atoms, —C≡CCH$_2$OH, —(CH$_2$)$_n$CH$_2$Y, —OR$^5$, —OCOR$^5$, —(CH$_2$)$_m$—CH=CH(CH$_2$)$_p$—R$^{6'}$ or —(CH$_2$)$_o$C≡CR$^7$;

wherein n=0, 1 or 2; m=0, 1, 2 or 3; p=0, 1 or 2; and o=0, 1 or 2;

wherein Y is a fluorine atom, a chlorine atom, a bromine atom, an iodine atom, a cyano group, an amino group, an azido group, a thiocyano group, —OR$^6$, —SR$^6$, —(CO)OR$^6$ or —(CO)SR$^6$;

wherein $R^6$ is a hydrogen atom, an alkyl radical having 1 to 10 carbon atoms, an aryl radical having 6 to 10 carbon atoms, an alkylaryl or arylalkyl radical each having 7 to 10 carbon atoms or —COR$^5$;

wherein $R^{6'}$ is a hydrogen atom, an alkyl radical having 1 to 10 carbon atoms, an aryl radical having 6 to 10 carbon atoms, an alkylaryl or arylalkyl radical each having 7 to 10 carbon atoms, —OR$^5$, —OC OR$^5$ or —COR$^5$;

wherein $R^7$ is a hydrogen atom, a fluorine atom, a chlorine atom, a bromine atom, an iodine atom, an alkyl radical having 1 to 10 carbon atoms, an aryl radical having 6 to 10 carbon atoms, an alkylaryl or arylalkyl radical each having 7 to 10 carbon atoms, —OR$^5$, —CH$_2$OR$^5$ or —OCOR$^5$; and wherein $R^5$ is a hydrogen atom, an alkyl group having 1 to 10 carbon atoms, an aryl group having 6 to 10 carbon atoms or an aralkyl or alkylaryl group each having 7 to 10 carbon atoms; or, alternatively, wherein $R^3$ and $R^4$ taken together form an optionally substituted five-member or six-member ring having at least one carbon atom and from 0 to 4 hetero atoms, and each of said hetero atoms is selected from the group consisting of oxygen, sulfur, selenium, tellurium, nitrogen, phosphorus, silicon and germanium;

said process comprising the steps of reacting a formic acid derivative of formula (III)

Nuc-(CO)—SR¹ (III), wherein Nuc is a nucleophile, in a solvent with a compound of formula (II):

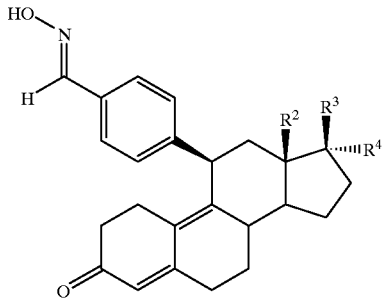

(II)

and converting to said compound of said formula (I).

17. The process as defined in claim 16, wherein said solvent is a tertiary amine and said reacting takes place at a temperature of from 20° C. to 80° C.

18. The process as defined in claim 17, wherein said reacting is carried out using chloroformic acid thioesters, said tertiary amine is pyridine or triethylamine and said temperature is from 20° C. to 40° C.

19. A pharmaceutical composition comprising a solid or liquid vehicle or diluent and at least one S-substituted 11β-benzaldoxime-estra-4,9-dien-carbonic acid thioester compound of the formula I:

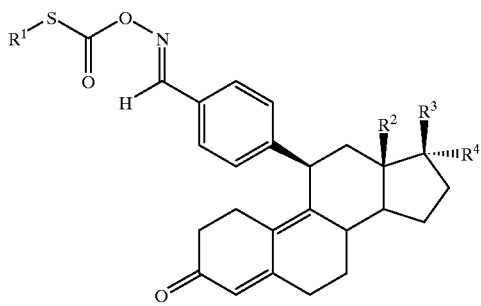

(I)

or a pharmaceutically acceptable salt thereof;
wherein
$R^1$ is an alkyl radical having 1 to 10 carbon atoms, an aryl radical having 6 to 10 carbon atoms or an alkylaryl or arylalkyl radical each having 7 to 10 carbon atoms;
$R^2$ is a hydrogen atom or an alkyl radical having 1 to 3 carbon atoms;
$R^3$ is a hydroxyl group, an O-alkyl group having 1 to 10 carbon atoms, an O-aryl group having 6 to 10 carbon atoms, an O-aralkyl group or an O-alkylaryl group, each having 7 to 10 carbon atoms, —OCOR⁵, —OCONHR⁵ or —OCOOR⁵;
$R^4$ is a hydrogen atom, an alkyl group having 1 to 10 carbon atoms, an aryl group having 6 to 10 carbon atoms, an aralkyl or alkylaryl group each having 7 to 10 carbon atoms, —C≡CCH₂OH, —(CH₂)ₙCH₂Y, —OR⁵, —OCOR⁵, —(CH₂)ₘ—CH=CH(CH₂)ₚ—R⁶' or —(CH₂)ₒC≡CR⁷;
wherein n=0, 1 or 2; m=0, 1, 2 or 3; p=0, 1 or 2; and o=0, 1 or 2;
wherein Y is a fluorine atom, a chlorine atom, a bromine atom, an iodine atom, a cyano group, an amino group, an azido group, a thiocyano group, —OR⁶, —SR⁶, —(CO)OR⁶ or —(CO)SR⁶;
wherein $R^6$ is a hydrogen atom, an alkyl radical having 1 to 10 carbon atoms, an aryl radical having 6 to 10 carbon atoms, an alkylaryl or arylalkyl radical each having 7 to 10 carbon atoms or —COR⁵;
wherein $R^{6'}$ is a hydrogen atom, an alkyl radical having 1 to 10 carbon atoms, an aryl radical having 6 to 10 carbon atoms, an alkylaryl or arylalkyl radical each having 7 to 10 carbon atoms, —OR⁵, —OC OR⁵ or —COR⁵;
wherein $R^7$ is a hydrogen atom, a fluorine atom, a chlorine atom, a bromine atom, an iodine atom, an alkyl radical having 1 to 10 carbon atoms, an aryl radical having 6 to 10 carbon atoms, an alkylaryl or arylalkyl radical each having 7 to 10 carbon atoms, —OR⁵, —CH₂OR⁵ or —OCOR⁵; and
wherein $R^5$ is a hydrogen atom, an alkyl group having 1 to 10 carbon atoms, an aryl group having 6 to 10 carbon atoms or an aralkyl or alkylaryl group each having 7 to 10 carbon atoms; or, alternatively,
wherein $R^3$ and $R^4$ taken together form an optionally substituted five-member or six-member ring having at least one carbon atom and from 0 to 4 hetero atoms, and each of said hetero atoms is selected from the group consisting of oxygen, sulfur, selenium, tellurium, nitrogen, phosphorus, silicon and germanium.

20. A pharmaceutical composition comprising a solid or liquid vehicle or diluent and at least one S-substituted 11β-benzaldoxime-estra-4,9-dien-carbonic acid thioester compound of the formula I, wherein said at least one S-substituted 11β-benzaldoxime-estra-4,9-dien-carbonic acid thioester compound of the formula I is selected from the group consisting of 4-[17β-methoxy-17α-(methoxymethyl)-3-oxoestra-4,9-dien-11β-yl]-benzaldehyde 1-(E)[O-(methylthio) carbonyl]oxime, 4-[17β-hydroxy-17α-(methoxymethyl)-3-oxoestra-4,9-dien-11β-yl]-benzaldehyde 1-(E)[O-(methylthio) carbonyl]oxime, 4-[17β-methoxy-17α-(methoxymethyl)-3-oxoestra-4,9-dien-11β-yl]-benzaldehyde 1-(E)[O-(ethylthio) carbonyl]oxime, 4-[17β-methoxy-17α-(methoxymethyl)-3-oxoestra-4,9-dien-11β-yl]-benzaldehyde 1-(Z)[O-(ethylthio) carbonyl]oxime, 4-[17β-methoxy-17α-(ethoxymethyl)-3-oxoestra-4,9-dien-11β-yl]-benzaldehyde 1-(E)[O-(ethylthio) carbonyl)oxime, 4-[17β-hydroxy-17α-(methoxymethyl)-3-oxoestra-4,9-dien-11β-yl]-benzaldehyde 1-(E)[O-(n-propylthio)-carbonyl]oxime, 4-[17β-methoxy-17α-(n-propoxymethyl)-3-oxoestra-4,9-dien-11β-yl]-benzaldehyde 1-(E)[O-(methylthio) carbonyl]oxime, 4-[17β-hydroxy-17α-(i-propoxymethyl)-3-oxoestra-4,9-dien-11β-yl]- benzaldehyde 1-(E)(O-(ethylthio) carbonyl]oxime, 4-[17β-hydroxy-17α-(methoxyethyl)-3-oxoestra-4,9-dien-11β-yl]-benzaldehyde 1-(E)[O-(ethylthio) carbonyl]oxime, 4-[17β-hydroxy-17α-Z-(3-hydroxypropenyl)-3-oxoestra-4,9-dien-11β-yl]-benzaldehyde 1-(E)[O-(methylthio)-carbonyl]oxime, 4-[17β-hydroxy-17α-E-(3-hydroxypropenyl)-3-oxoestra-4,9-dien-11β-yl]-benzaldehyde 1-(E)[O-(methylthio) carbonyl]oxime, 4-[17β-methoxy-17α-(3-hydroxy-1-propinyl)-3-oxoestra-4,9-dien-11β-yl]-benzaldehyde 1-(E)[O-(ethylthio)carbonyl]oxime, 4-[17β-hydroxy-17α-(azidomethyl)-3-oxoestra-4,9-dien-11β-yl]-benzaldehyde 1-(E)-[O-(methylthio)carbonyl]oxime, 4-[17β-hydroxy-17α-(chloromethyl)-3-oxoestra-4,9-dien-11β-yl]-benzaldehyde 1-(E)[O-(ethylthio)carbonyl]oxime, 4-[17β-ethoxy-17α-(chloromethyl)-3-oxoestra-4,9-dien-11β-yl]-benzaldehyde 1-(E)[O-(methylthio)carbonyl]oxime 4-[17β-hydroxy-17α-(cyanomethyl)-3-oxoestra-4,9-dien-11β-yl]-benzaldehyde 1-(E)[O-(ethylthio)carbonyl]oxime, 4-[17β-hydroxy-17α-(ethylthiomethyl)-3-oxoestra-4,9-dien-11β-yl]-benzaldehyde 1-(E)[O-(ethylthio)carbonyl]oxime, 4-[17β-hydroxy-17α-(ethylthiomethyl)-3-oxoestra-4,9-dien-11β-yl]-benzaldehyde 1-(E)[O-(methylthio)carbonyl]oxime, 4-[17β-ethoxy-17α-(methylthiomethyl)-3-oxoestra-4,9-dien-11β-yl]-benzaldehyde 1-(E)[O-(ethylthio)carbonyl]oxime, 4-[17β-hydroxy-17α-[(ethylthio)carbonyl)methyl)-3-oxoestra-4,9-dien-11β-yl]benzaldehyde 1-(E)[O-(ethylthio)carbonyl]oxime, 4-[17β-hydroxy-17α-(aminomethyl)-3-oxoestra-4,9-dien-11β-yl]-benzaldehyde 1-(E)[O-(ethylthio)carbonyl]oxime and (17R)-4-(3-oxoestra-4,9-dien-17-spiro-5'-oxazolidin-2'-on- 11β-yl)-benzaldehyde 1-(E)-[O-(ethylthio)-carbonyl]oxime.

21. A method of treating a female having at least one condition selected from the group consisting of endometriosis, uterus myomatosus, dysmenorrhea, premenstrual syndrome, for induction of reversible amenorrhea without estrogen deficit and for menopausal hormone replacement therapy, said method comprising administering an effective amount of at least one compound to said female, wherein said at least one compound consists of at least one S-substituted 11β-benzaldoxime-estra-4,9-dien-carbonic acid thioester compound of the formula I:

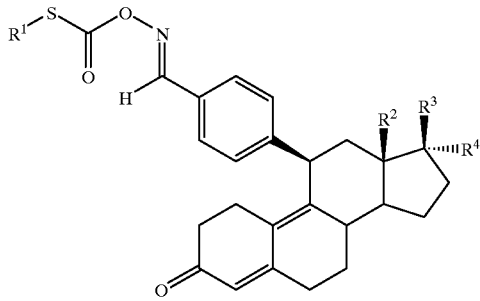

(I)

or a pharmaceutically acceptable salt thereof;
wherein
$R^1$ is an alkyl radical having 1 to 10 carbon atoms, an aryl radical having 6 to 10 carbon atoms or an alkylaryl or arylalkyl radical each having 7 to 10 carbon atoms;
$R^2$ is a hydrogen atom or an alkyl radical having 1 to 3 carbon atoms;

$R^3$ is a hydroxyl group, an O-alkyl group having 1 to 10 carbon atoms, an O-aryl group having 6 to 10 carbon atoms, an O-aralkyl group or an O-alkylaryl group, each having 7 to 10 carbon atoms, —OCOR$^5$, —OCONHR$^5$or —OCOOR$^5$;

$R^4$ is a hydrogen atom, an alkyl group having 1 to 10 carbon atoms, an aryl group having 6 to 10 carbon atoms, an aralkyl or alkylaryl group each having 7 to 10 carbon atoms, —C≡CCH$_2$OH, —(CH$_2$)$_n$CH$_2$Y, —OR$^5$, —OCOR$^5$, —(CH$_2$)$_m$—CH=CH(CH$_2$)$_p$—R$^{6'}$ or —(CH$_2$)$_o$C≡CR$^7$;
wherein n=0, 1 or 2; m=0, 1, 2 or 3; p=0, 1 or 2; and o=0, 1 or 2;
wherein Y is a fluorine atom, a chlorine atom, a bromine atom, an iodine atom, a cyano group, an amino group, an azido group, a thiocyano group, —OR$^6$, —SR$^6$, —(CO)OR$^6$ or —(CO)SR$^6$;
wherein $R^6$ is a hydrogen atom, an alkyl radical having 1 to 10 carbon atoms, an aryl radical having 6 to 10 carbon atoms, an alkylaryl or arylalkyl radical each having 7 to 10 carbon atoms or —COR$^5$;
wherein $R^{6'}$ is a hydrogen atom, an alkyl radical having 1 to 10 carbon atoms, an aryl radical having 6 to 10 carbon atoms, an alkylaryl or arylalkyl radical each having 7 to 10 carbon atoms, —OR$^5$, —OC OR$^5$ or —COR$^5$;
wherein $R^7$ is a hydrogen atom, a fluorine atom, a chlorine atom, a bromine atom, an iodine atom, an alkyl radical having 1 to 10 carbon atoms, an aryl radical having 6 to 10 carbon atoms, an alkylaryl or arylalkyl radical each having 7 to 10 carbon atoms, —OR$^5$, —CH$_2$OR$^5$ or —OCOR$^5$; and
wherein $R^5$ is a hydrogen atom, an alkyl group having 1 to 10 carbon atoms, an aryl group having 6 to 10 carbon atoms or an aralkyl or alkylaryl group each having 7 to 10 carbon atoms; or, alternatively,
wherein $R^3$ and $R^4$ taken together form an optionally substituted five-member or six-member ring having at least one carbon atom and from 0 to 4 hetero atoms, and each of said hetero atoms is selected from the group consisting of oxygen, sulfur, selenium, tellurium, nitrogen, phosphorus, silicon and germanium.

22. A method of treating a female having at least one condition selected from the group consisting of endometriosis, uterus myomatosus, dysmenorrhea, premenstrual syndrome, for induction of reversible amenorrhea without estrogen deficit and for menopausal hormone replacement therapy, said method comprising administering an effective amount of at least one compound to said female, wherein said at least one compound is selected from the group consisting of 4-[17β-methoxy-17α-(methoxymethyl)-3-oxoestra-4,9-dien-11β-yl]-benzaldehyde 1-(E)[O-(methylthio)carbonyl]oxime, 4-[17β-hydroxy-17α-(methoxymethyl)-3-oxoestra-4,9-dien-11β-yl]-benzaldehyde 1-(E)[O-(methylthio)carbonyl]oxime, 4-[17β-methoxy-17α-(methoxymethyl)-3-oxoestra-4,9-dien-11β-yl]-benzaldehyde 1-(E)[O-(ethylthio)carbonyl]oxime, 4-[17β-methoxy-17α-(methoxymethyl)-3-oxoestra-4,9-dien-11β-yl]-benzaldehyde 1-(Z)[O-(ethylthio)carbonyl]oxime, 4-[17β-methoxy-17α-(ethoxymethyl)-3-oxoestra-4,9-dien-11β-yl]-benzaldehyde 1-(E)[O-(ethylthio)carbonyl]oxime, 4-[17β-hydroxy-17α-(methoxymethyl)-3-oxoestra-4,9-dien-11β-yl]-benzaldehyde 1-(E)[O-(n-propylthio)-carbonyl]oxime, 4-[17β-methoxy-17α-(n-propoxymethyl)-3-oxoestra-4,9-dien-11β-yl]-benzaldehyde 1-(E)[O-(methylthio)carbonyl]oxime, 4-[17β-hydroxy-17α-(i-propoxymethyl)-3-oxoestra-4,9-dien-11β-yl]-benzaldehyde 1-(E)(O-(ethylthio)carbonyl]oxime, 4-[17β-hydroxy-17α-(methoxyethyl)-3-oxoestra-4,9-dien-11β-yl]-benzaldehyde 1-(E)[O-(ethylthio)carbonyl]oxime, 4-[17 β-hydroxy-17-Z-(3-hydroxypropenyl)-3-oxoestra-4,9-dien-11β-yl]-benzaldehyde 1-(E)[O-(methylthio)-carbonyl]oxime, 4-[17β-hydroxy-17α-E-(3-hydroxypropenyl)-3-oxoestra-4,9-dien-11β-yl]-benzaldehyde 1-(E)[O-(methylthio)carbonyl]oxime, 4-[17β-methoxy-17α-(3-hydroxy-1-propinyl)-3-oxoestra-4,9-dien-11β-yl]-benzaldehyde 1-(E)[O-(ethylthio)carbonyl]oxime, 4-[17β-hydroxy-17α-(azidomethyl)-3-oxoestra-4,9-dien-11β-yl]-benzaldehyde 1-(E)-[O-(methylthio)carbonyl]oxime, 4-[17β-hydroxy-17α-(chloromethyl)-3-oxoestra-4,9-dien-11β-yl]-benzaldehyde 1-(E)[O-(ethylthio)carbonyl]oxime, 4-[17β-ethoxy-17α-(chloromethyl)-3-oxoestra-4,9-dien-11β-yl]-benzaldehyde 1-(E)[O-(methylthio)carbonyl)oxime 4-[17β-hydroxy-17α-(cyanomethyl)-3-oxoestra-4,9-dien-11β-yl]-benzaldehyde 1-(E)[O-(ethylthio)carbonyl]oxime, 4-[17β-hydroxy-17α-(ethylthiomethyl)-3-oxoestra-4,9-dien-11β-yl]-benzaldehyde 1-(E)[O-(ethylthio)carbonyl]oxime, 4-[17β-hydroxy-17α-(ethylthiomethyl)-3-oxoestra-4,9-dien-11-yl]-benzaldehyde 1-(E)[O-(methylthio)carbonyl]oxime, 4-[17β-ethoxy-17α-(methylthiomethyl)-3-oxoestra-4,9-dien-11β-yl]-benzaldehyde 1-(E)[O-(ethylthio)carbonyl]oxime, 4-[17β-hydroxy-17α-[(ethylthio)carbonyl)methyl-3-oxoestra-4,9-dien-11β-yl]benzaldehyde 1-(E)[O-(ethylthio)carbonyl]oxime, 4-[17β-hydroxy-17α-(aminomethyl)-3-oxoestra-4,9-dien-11β-yl]-benzaldehyde 1-(E)[O-(ethylthio)carbonyl]oxime and (17R)-4-(3-oxoestra-4,9-dien-17-spiro-5'-oxazolidin-2'-on-11β-yl)-benzaldehyde 1-(E)-[O-(ethylthio)carbonyl]oxime.

23. The method as defined in claim 21 or 22, for said menopausal hormone replacement therapy and further comprising administering estrogens with said at least one compound to said female.

24. A method of making a contraceptive composition, said method comprising using at least one S-substituted 11β-benzaldoxime-estra-4,9-dien-carbonic acid thioester compound of the formula I:

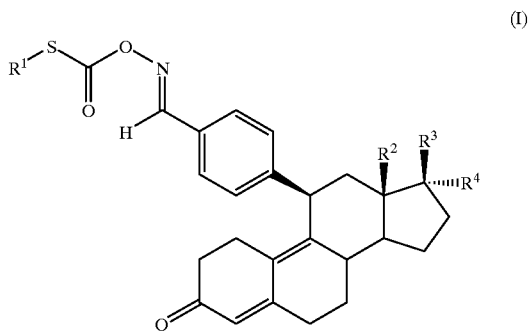

or a pharmaceutically acceptable salt thereof;
wherein $R^1$ is an alkyl radical having 1 to 10 carbon atoms, an aryl radical having 6 to 10 carbon atoms or an alkylaryl or arylalkyl radical each having 7 to 10 carbon atoms;

$R^2$ is a hydrogen atom or an alkyl radical having 1 to 3 carbon atoms;

$R^3$ is a hydroxyl group, an O-alkyl group having 1 to 10 carbon atoms, an O-aryl group having 6 to 10 carbon atoms, an O-aralkyl group or an O-alkylaryl group, each having 7 to 10 carbon atoms, —$OCOR^5$, —$OCONHR^5$ or —$OCOOR^5$;

$R^4$ is a hydrogen atom, an alkyl group having 1 to 10 carbon atoms, an aryl group having 6 to 10 carbon atoms, an aralkyl or alkylaryl group each having 7 to 10 carbon atoms, —$C{\equiv}CCH_2OH$, —$(CH_2)_nCH_2Y$, —$OR^5$, —$OCOR^5$, —$(CH_2)_m$—$CH{=}CH(CH_2)_p$—$R^{6'}$ or —$(CH_2)_oC{\equiv}CR^7$;

wherein n=0, 1 or 2; m=0, 1, 2 or 3; p=0, 1 or 2; and o=0, 1 or 2;

wherein Y is a fluorine atom, a chlorine atom, a bromine atom, an iodine atom, a cyano group, an amino group, an azido group, a thiocyano group, —$OR^6$, —$SR^6$, —$(CO)OR^6$ or —$(CO)SR^6$;

wherein $R^6$ is a hydrogen atom, an alkyl radical having 1 to 10 carbon atoms, an aryl radical having 6 to 10 carbon atoms, an alkylaryl or arylalkyl radical each having 7 to 10 carbon atoms or —$COR^5$;

wherein $R^{6'}$ is a hydrogen atom, an alkyl radical having 1 to 1 0 carbon atoms, an aryl radical having 6 to 10 carbon atoms, an alkylaryl or arylalkyl radical each having 7 to 10 carbon atoms, —$OR^5$, —$OC\,OR^5$ or —$COR^5$;

wherein $R^7$ is a hydrogen atom, a fluorine atom, a chlorine atom, a bromine atom, an iodine atom, an alkyl radical having 1 to 10 carbon atoms, an aryl radical having 6 to 10 carbon atoms, an alkylaryl or arylalkyl radical each having 7 to 10 carbon atoms, —$OR^5$, —$CH_2OR^5$ or —$OCOR^5$; and wherein $R^5$ is a hydrogen atom, an alkyl group having 1 to 10 carbon atoms, an aryl group having 6 to 10 carbon atoms or an aralkyl or alkylaryl group each having 7 to 10 carbon atoms; or, alternatively, wherein $R^3$ and $R^4$ taken together form an optionally substituted five-member or six-member ring having at least one carbon atom and from 0 to 4 hetero atoms, and each of said hetero atoms is selected from the group consisting of oxygen, sulfur, selenium, tellurium, nitrogen, phosphorus, silicon and germanium.

25. A method of making a contraceptive composition, said method comprising using at least one S-substituted 11β- benzaldoxime-estra-4,9-dien-carbonic acid thioester compound selected from the group consisting of:

- 4-[17β-methoxy-17α-(methoxymethyl)-3-oxoestra-4,9-dien- 11β-yl]-benzaldehyde 1-(E)[O-(methylthio)carbonyl]oxime,
- 4-[17β-hydroxy-17α-(methoxymethyl)-3-oxoestra-4,9-dien-11β-yl]-benzaldehyde 1-(E)[O-(methylthio)carbonyl]oxime,
- 4-[17β-methoxy-17α-(methoxymethyl)-3-oxoestra-4,9-dien-11β-yl]-benzaldehyde 1-(E)[O-(ethylthio)carbonyl]oxime,
- 4-[17β-methoxy-17α-(methoxymethyl) -3-oxoestra-4,9-dien-11β-yl]-benzaldehyde 1-(Z)[O-(ethylthio)carbonyl]oxime,
- 4-[17β-methoxy-17α-(ethoxymethyl)-3-oxoestra-4,9-dien-11β-yl]-benzaldehyde 1-(E)[O-(ethylthio)carbonyl)oxime,
- 4-[17β-hydroxy-17α-(methoxymethyl) -3-oxoestra-4,9-dien-11β-yl]-benzaldehyde 1-(E)[O-(n-propylthio)-carbonyl]oxime,
- 4-[17β-methoxy-17α-(n-propoxymethyl)-3-oxoestra-4,9-dien-11β-yl]-benzaldehyde 1-(E)[O-(methylthio)carbonyl]oxime,
- 4-[17β-hydroxy-17α-(i-propoxymethyl)-3-oxoestra-4,9-dien-11β-yl]-benzaldehyde 1-(E)(O-(ethylthio)carbonyl]oxime,
- 4-[17β-hydroxy-17α-(methoxyethyl)-3-oxoestra-4,9-dien-11β-yl]-benzaldehyde 1-(E)[O-(ethylthio)carbonyl]oxime,
- 4-[17β-hydroxy-17α-Z-(3-hydroxypropenyl)-3-oxoestra-4,9-dien-11β-yl]-benzaldehyde 1-(E)[O-(methylthio)-carbonyl]oxime,
- 4-[17β-hydroxy-17α-E-(3-hydroxypropenyl)-3-oxoestra-4,9-dien-11β-yl]-benzaldehyde 1-(E)[O-(methylthio)carbonyl]oxime,
- 4-[17β-methoxy-17α-(3-hydroxy-1-propinyl)-3-oxoestra-4,9-dien-11β-yl]-benzaldehyde 1-(E)[O-(ethylthio)carbonyl]oxime,
- 4-[17β-hydroxy-17α-(azidomethyl)-3-oxoestra-4,9-dien-11β-yl]-benzaldehyde 1-(E)-[O-(methylthio)carbonyl]oxime,
- 4-[17β-hydroxy-17α-(chloromethyl)-3-oxoestra-4,9-dien-11-yl]-benzaldehyde 1-(E)[O-(ethylthio)carbonyl]oxime,
- 4-[17β-ethoxy-17α-(chloromethyl)-3-oxoestra-4,9-dien-11β-yl]-benzaldehyde 1-(E)[O-(methylthio)carbonyl)oxime
- 4-[17β-hydroxy-17α-(cyanomethyl)-3-oxoestra-4,9-dien-11β-yl]-benzaldehyde 1-(E)[O-(ethylthio)carbonyl]oxime,
- 4-[17β-hydroxy-17α-(ethylthiomethyl)-3-oxoestra-4,9-dien-11β-yl]-benzaldehyde 1-(E)[O-(ethylthio)carbonyl]oxime,
- 4-[17β-hydroxy-17α-(ethylthiomethyl)-3-oxoestra-4,9-dien-11-yl]-benzaldehyde 1-(E)[O-(methylthio)carbonyl]oxime,
- 4-[17β-ethoxy-17α-(methylthiomethyl)-3-oxoestra-4,9-dien-11β-yl]-benzaldehyde 1-(E)[O-(ethylthio)carbonyl]oxime,
- 4-[17β-hydroxy-17α-[(ethylthio)carbonyl)methyl-3-oxoestra-4,9-dien-11β-yl]benzaldehyde 1-(E)[O-(ethylthio)carbonyl]oxime,
- 4-[17β-hydroxy-17α-(aminomethyl)-3-oxoestra-4,9-dien-11β-yl]-benzaldehyde 1-(E)[O-(ethylthio)carbonyl]oxime and
- (17R)-4-(3-oxoestra-4,9-dien-17-spiro-5'-oxazolidin-2'-on-11β-yl)-benzaldehyde 1-(E)-[O-(ethylthio)carbonyl]oxime.

* * * * *